(12) United States Patent
Chan

(10) Patent No.: US 6,299,642 B1
(45) Date of Patent: Oct. 9, 2001

(54) BONE CEMENT PLUG FOR DEPLOYMENT IN A BONE CANAL

(76) Inventor: Kwan-Ho Chan, 4803 1st Pl., Lubbock, TX (US) 79416

( * ) Notice: Subject to any disclaimer, the term of this patent is extended or adjusted under 35 U.S.C. 154(b) by 0 days.

(21) Appl. No.: 09/243,029

(22) Filed: Feb. 3, 1999

Related U.S. Application Data

(63) Continuation-in-part of application No. 08/800,928, filed on Feb. 13, 1997, now Pat. No. 5,935,169.

(51) Int. Cl.[7] ............................... A61F 2/42; A61F 5/04; A61B 17/56; F16B 13/04
(52) U.S. Cl. .................................. 623/16.11; 623/17.11; 623/17.15; 623/17.16; 606/60; 606/63; 606/95; 411/55; 411/60
(58) Field of Search ..................... 623/16.11, 17.11, 623/17.15, 17.16; 606/60–63, 95; 411/55, 60, 63, 64, 72, 178

(56) References Cited

U.S. PATENT DOCUMENTS

| | | | |
|---|---|---|---|
| 4,523,587 | * | 6/1985 | Frey ........................................ 128/92 |
| 5,078,746 | * | 1/1992 | Garner ..................................... 623/16 |
| 5,360,450 | * | 11/1994 | Giannini .................................. 623/21 |
| 5,746,557 | * | 5/1998 | Kaibach .................................. 411/60 |
| 5,762,451 | * | 6/1998 | Stankus et al. .................... 405/259.1 |
| 5,766,178 | * | 6/1998 | Michielli et al. ....................... 606/95 |
| 5,791,846 | * | 8/1998 | Mayr ...................................... 411/60 |

* cited by examiner

Primary Examiner—Corrine McDermott
Assistant Examiner—Choon Koh
(74) Attorney, Agent, or Firm—Pandiscio & Pandiscio

(57) ABSTRACT

A core for forming a bone cement plug for deployment in a bone canal, the core including a base portion defining a bore having internal teeth therein and extending axially and distally from a proximal end of the base portion. A first leg portion depends from and extends distally from the base portion, the first leg portion having a first protrusion at a distal end thereof extending outwardly from an outside wall of the first leg portion through a first arc, and a second leg portion depends from and extends distally from the base portion, the second leg portion having a second protrusion at a distal end thereof extending outwardly from an outside wall of the second leg portion through a second arc and oppositely to the first arc. The toothed bore of the base portion is adapted to receive an expander member to wedge apart the first and second leg portions to expand the core widthwise to secure the core in the bone canal.

25 Claims, 25 Drawing Sheets

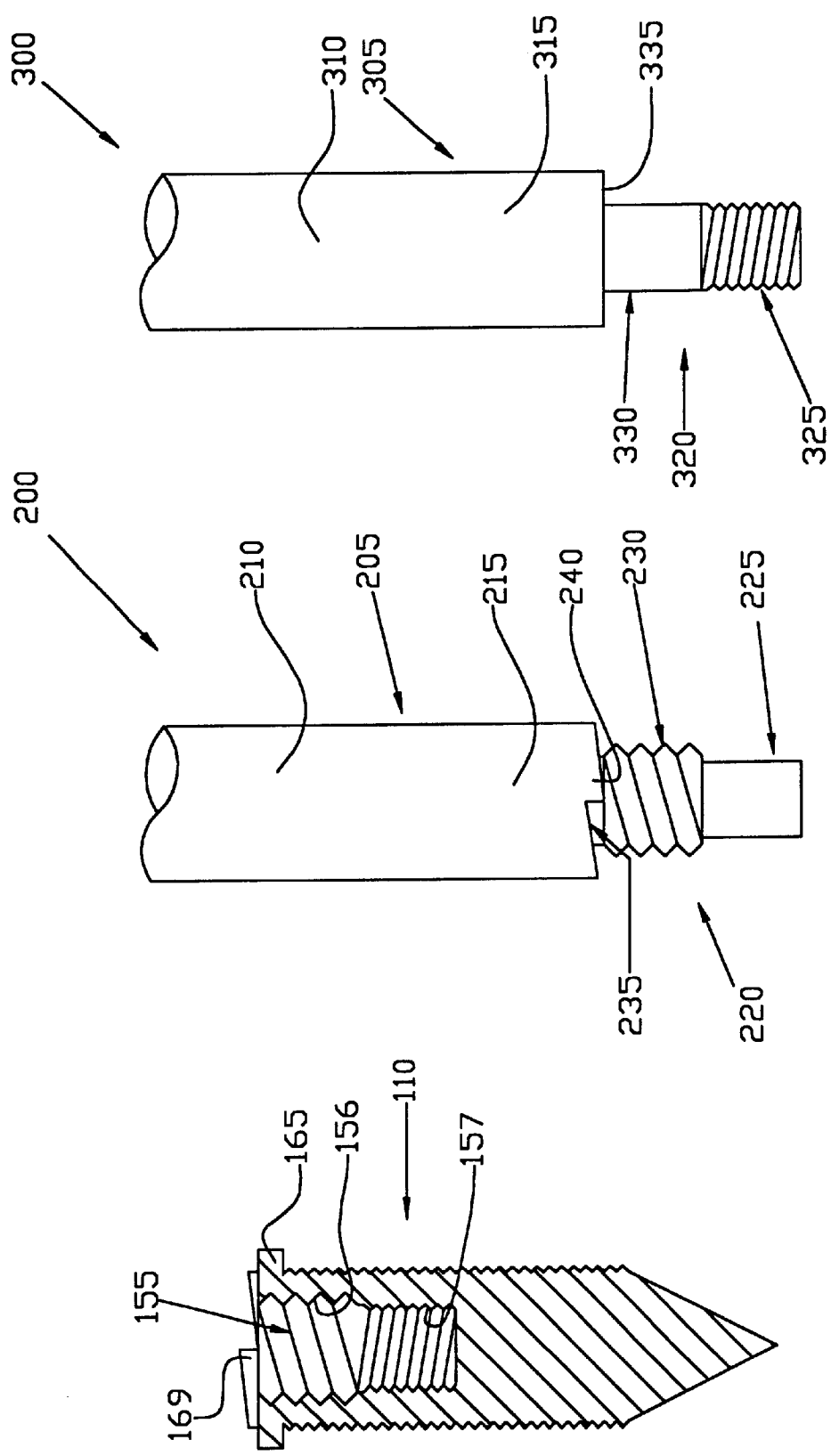

Insert Extractor tip into Expander Screw

Rotate Extractor anticlockwise till it is fully engaged to the Expander Screw

Continue to rotate Extractor anticlockwise to partially back out the Expander Screw allowing the core of the Plug to collapse Pull Plug out of the femoral canal

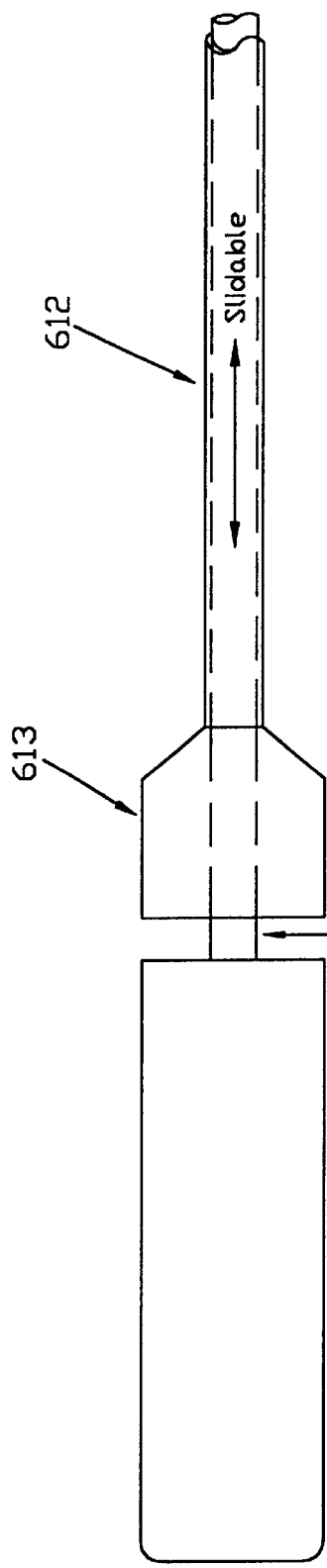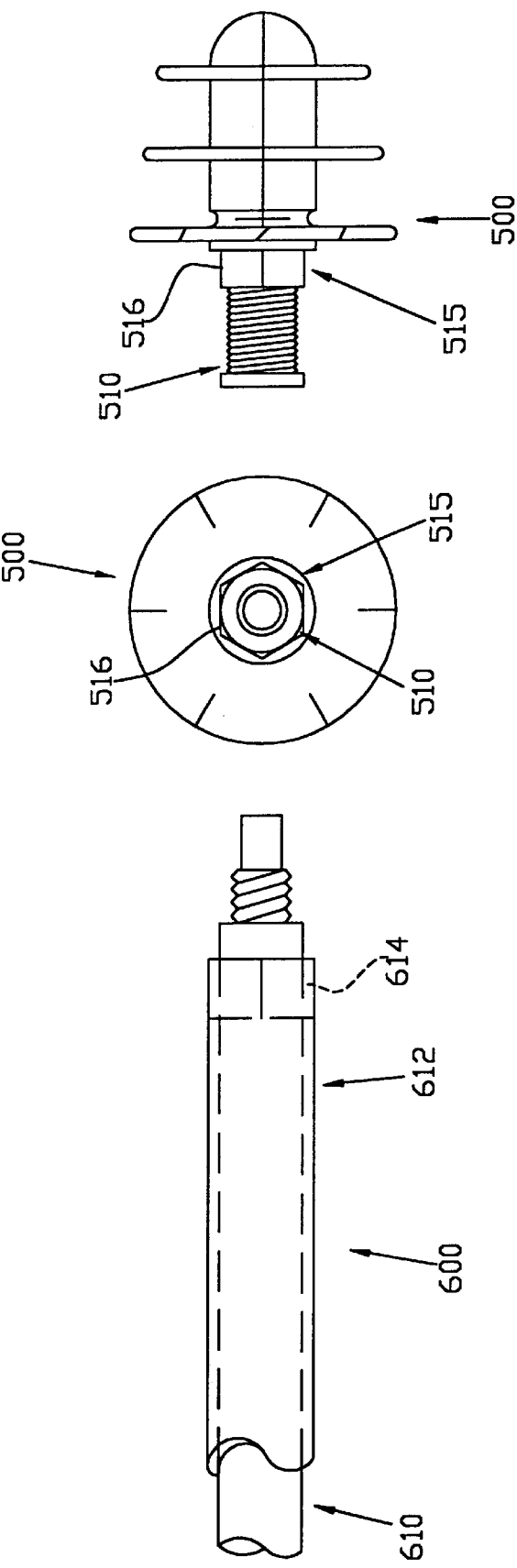

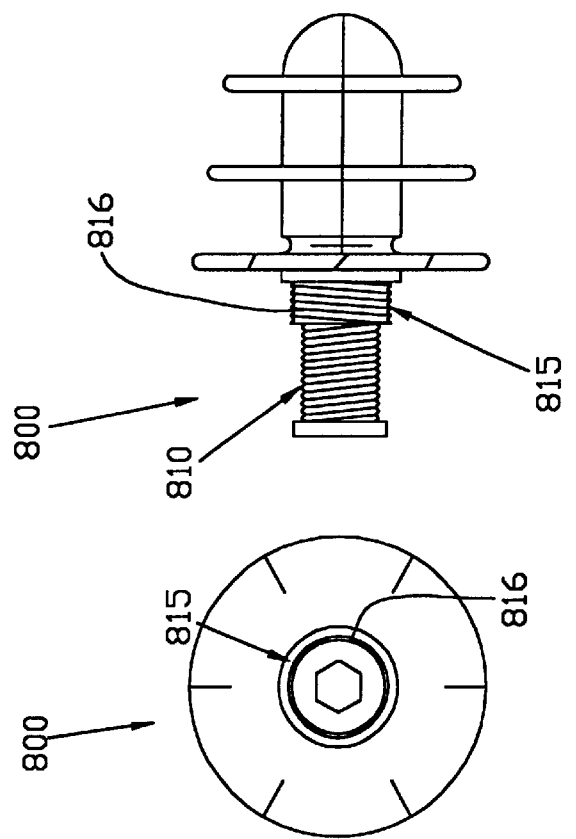
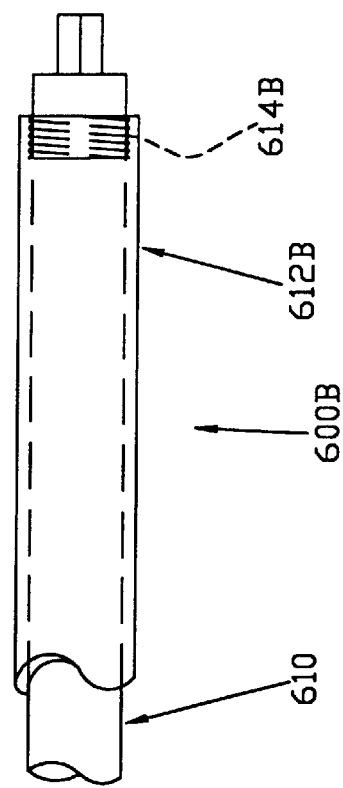
Fig. 56C
Fig. 56B
Fig. 56A

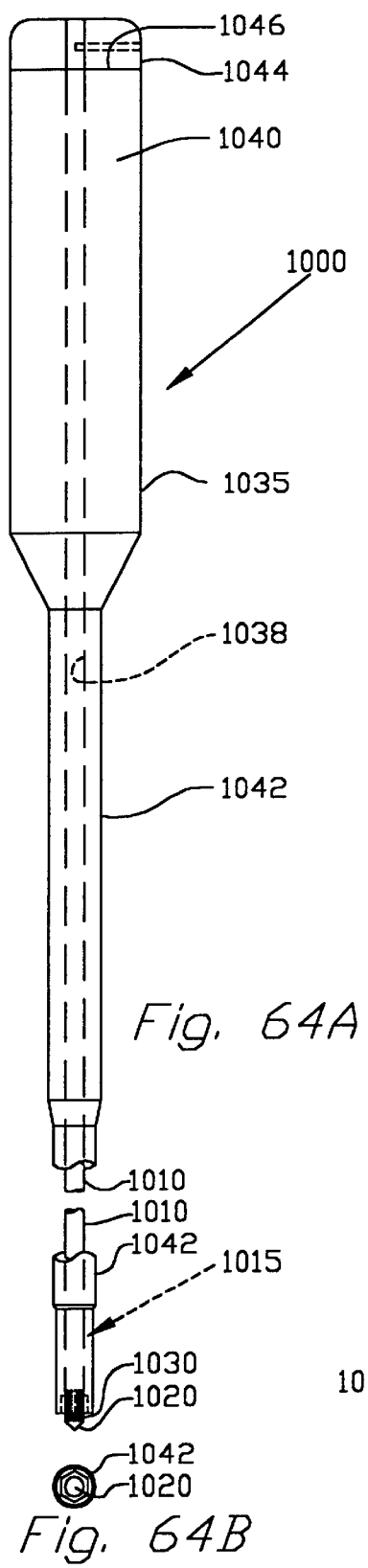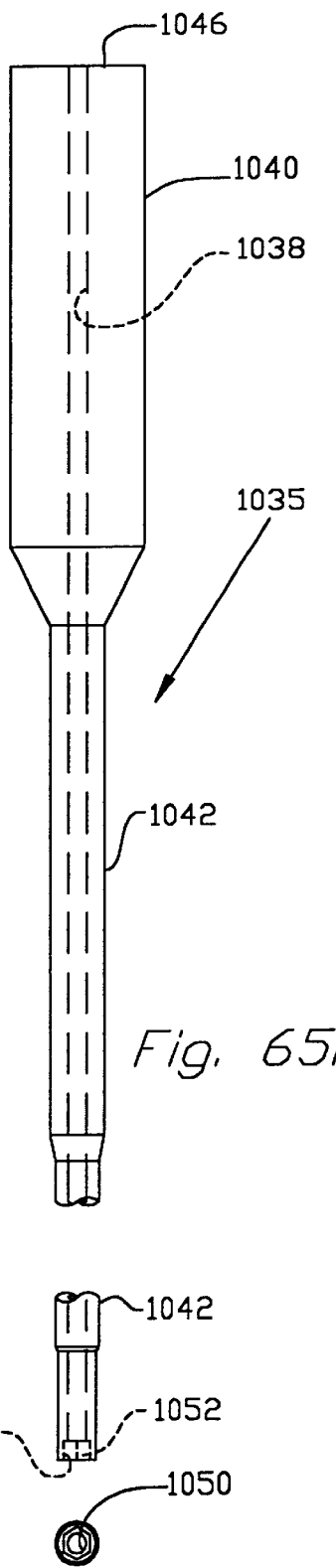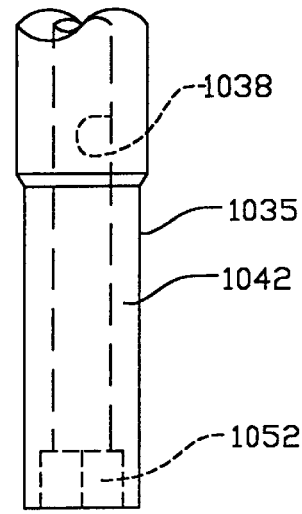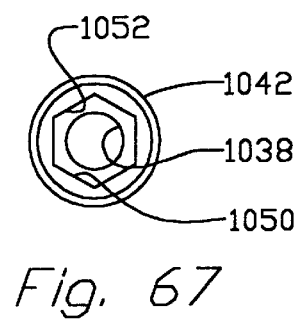
Fig. 64A
Fig. 64B
Fig. 65A
Fig. 65B
Fig. 66
Fig. 67

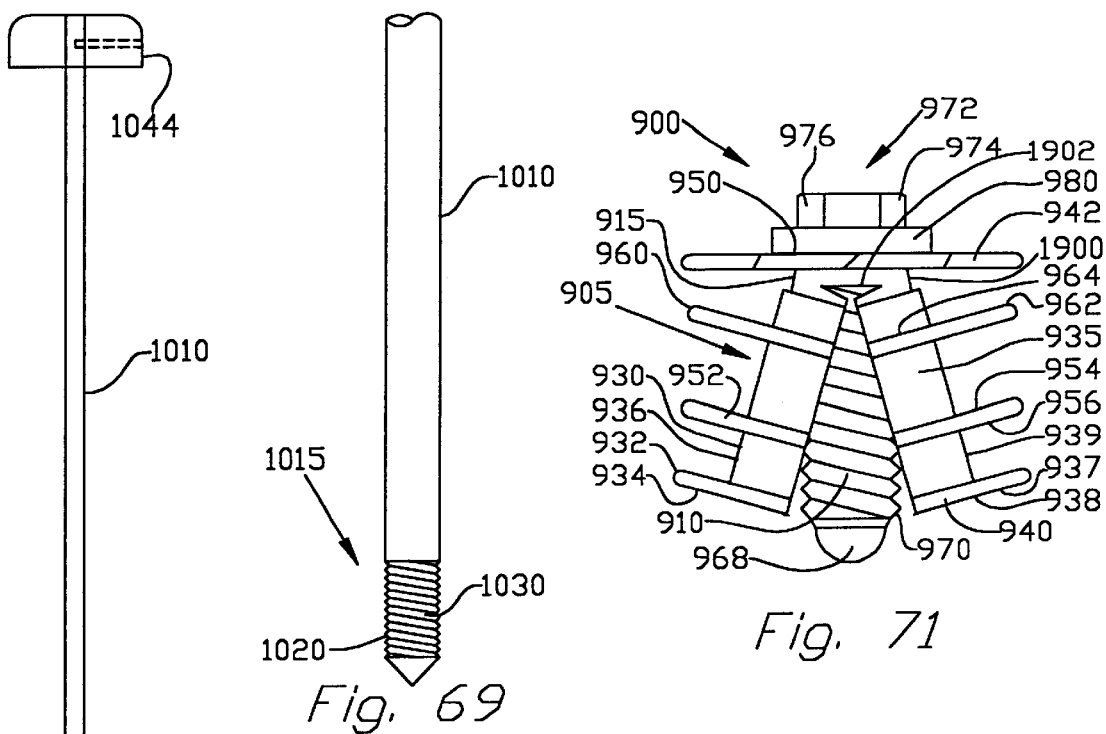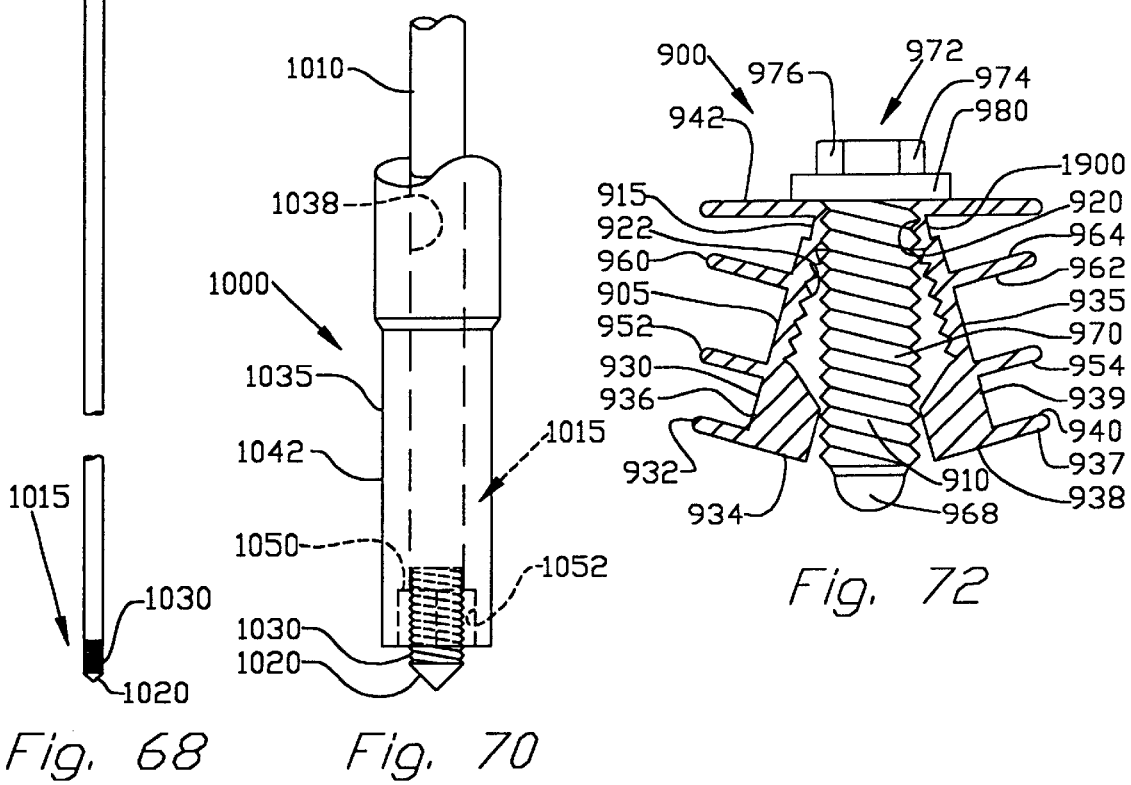

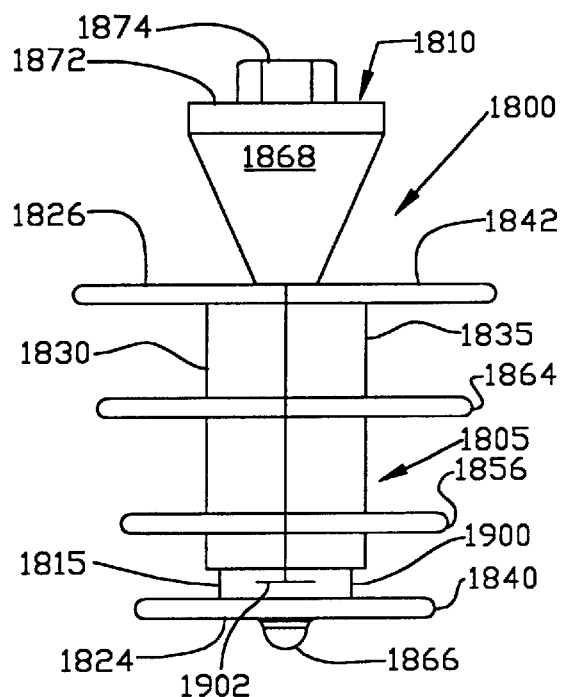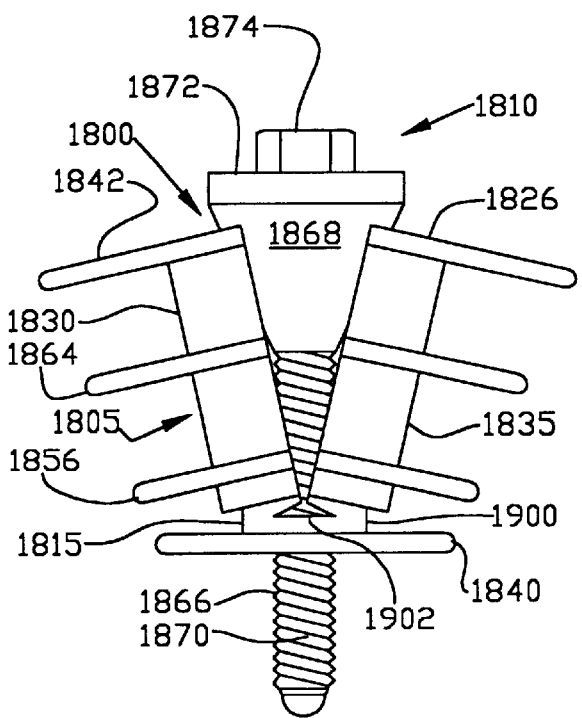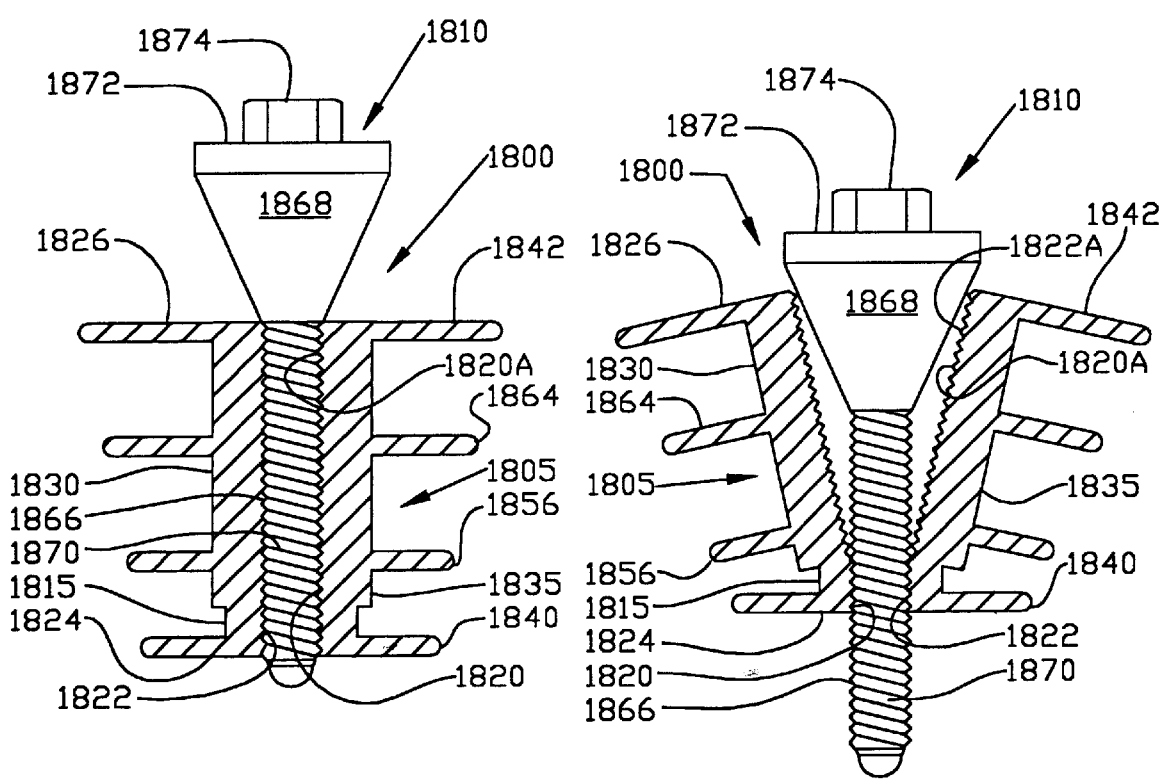
Fig. 102
Fig. 104
Fig. 103
Fig. 105

BONE CEMENT PLUG FOR DEPLOYMENT IN A BONE CANAL

CROSS-REFERENCE TO RELATED APPLICATION

This is a continuation-in-part of U.S. patent application Ser. No. 08/800,928, filed Feb. 13, 1997 now U.S. Pat. No. 5,935,169, by Kwan-Ho Chan for BONE CEMENT PLUG FOR DEPLOYMENT IN A BONE CANAL.

FIELD OF THE INVENTION

This invention relates to surgical apparatus and procedures in general, and more particularly to bone cement plugs of the sort used in conjunction with bone cement dispensers to compact bone cement into bone canals during total joint replacement surgeries.

BACKGROUND OF THE INVENTION

Bone cement plugs are well known in the art. Such devices are generally used in conjunction with bone cement dispensers to compact bone cement into a bone canal before fixing a prosthetic device in that bone canal. By way of example, bone cement plugs are commonly used in conjunction with bone cement dispensers to compact bone cement into the intramedullary canal of the femur before fixing the femoral stem of an artificial hip in that canal.

More particularly, in total joint replacement surgeries, such as hip and shoulder replacements, bone cement is commonly used to fix the stems of the prosthetic devices into the medullary canals of the joint's bones. In this respect, it has generally been found that a prosthetic device will be more securely fixed in a bone canal if the bone cement is well packed into the bone canal before the stem of the prosthetic device is positioned in the bone canal.

To this end, after initial preparation and cleaning of the bone canal, the distal portion of the canal is generally occluded with a plug. The bone cement plug serves to limit uncontrolled flow of bone cement into the distal portion of the bone canal. Ideally, the bone cement plug limits the column of bone cement to about 1 to 2 cm beyond the distal tip of the stem of the prosthesis. After the plug has been set at the distal portion of the bone canal, the bone cement is injected into the distal-most part of the occluded bone canal, adjacent to the plug, using a bone cement dispenser having a long nozzle. The bone canal is then filled with bone cement in a retrograde fashion, by withdrawing the nozzle of the bone cement dispenser from the distal end of the bone canal to the proximal end of the bone canal, as the cement issues from the nozzle. Such retrograde filling helps avoid trapping air in the distal-most part of the bone canal.

After the bone canal has been filled with bone cement, a bone canal pressurizer is then connected to the bone cement dispenser. The pressurizer is pressed against the open end of the bone so as to occlude the proximal end of the bone canal. More cement is then injected into the bone canal through the pressurizer and under pressure. Under such pressurization, the cement in the bone canal intrudes into the interstices of the inner surface of the bone wall defining the bone canal. When the bone cement thereafter sets, a micro-interlock is established between the cement and the irregularities of the inner surface of the bone wall. This significantly enhances fixation of the prosthetic device in the bone canal.

Ideally, a bone cement plug should be easy to deploy at the desired depth in the bone canal, effective in closing off that bone canal and, in the event that the bone cement plug subsequently needs to be removed, easy to retrieve from the distal end of the bone canal. The bone cement plug must also be bio-compatible with the patient. Furthermore, the bone cement plug should be inexpensive to produce.

A variety of bone cement plugs are known in the art.

See, for example, the bone cement plugs described and illustrated in U.S. Pat. Nos. 4,245,359; 4,276,659; 4,293,962; 4,302,855; 4,344,190; 4,447,915; 4,627,434; 4,686,973; 4,697,584; 4,745,914; 4,936,859; 4,950,295; 4,994,085; 5,061,287; 5,078,746; 5,092,891; 5,376,120; and 5,383,932.

See also, for example, the bone cement plug described and illustrated in British Patent Document No. 2,253,564A.

See also, for example, the publication entitled "Polyethylene medullary plug according to Stuhmer/Weber" distributed by ALLO PRO AG of Switzerland.

See also related apparatus described and illustrated in U.S. Pat. Nos. 4,011,602; 4,523,587; and 4,904,267.

See also related apparatus described and illustrated in European Patent Document No. 0,006,408 B1; and PCT Patent Document No. WO 94/15544.

Unfortunately, however, all of the bone cement plugs developed to date tend to suffer from one or more significant disadvantages.

More particularly, in general, the fixation of the bone cement plug depends on the friction established between the wall of the bone canal and the bone cement plug. Currently, the most common surgical technique is to first measure the size of the prepared bone canal. This typically involves sequentially inserting a number of "sizers" into the bone canal so as to determine the gross cross-sectional diameter of the canal at the desired depth. Having thus determined the size of the bone canal, an over-sized plug is then inserted into the canal so as to occlude the bone canal at the desired depth.

Unfortunately, however, if the bone cement plug is not sufficiently over-sized relative to the diameter of the bone canal, or if the plug is too easily deformable, the bone cement plug's engagement with the wall of the bone canal will be less than optimal, and this may lead to complications. In particular, during the aforementioned pressurization phase, or during the subsequent insertion of the prosthesis, the increased pressure of the bone cement can cause the insufficiently-anchored plug to migrate distally. On the other hand, if the bone cement plug is too greatly over-sized, and/or if the plug is overly rigid, the bone cement plug cannot be inserted into the bone canal to the desired depth. Also, excessively forceful insertion of the bone cement plug into the bone canal can cause the wall of the bone canal to fracture in some circumstances.

In addition to the foregoing, many of the current bone cement plugs cannot be adequately anchored against the wall of the bone canal if the plug needs to be located distally of the isthmus, i.e., against a portion of the bone canal located distally of the narrowest part of the canal. This is because the largest possible size of the bone cement plug is limited by the need for the bone cement plug to pass through the narrowest part of the bone canal. In other words, in this situation, a smaller than desired plug size must be used.

Various expandable plugs have been designed to address the foregoing issues. However, such known expandable bone cement plugs suffer from a number of drawbacks, such as difficulty in manufacturing, inadequate fixation, the complexity of their associated insertion tools, etc.

OBJECTS OF THE INVENTION

Accordingly, the primary object of the present invention is to provide an improved bone cement plug for deployment in a bone canal.

Another object of the present invention is to provide a bone cement plug which is easy to deploy at the desired depth in the bone canal, effective in closing off that bone canal and, in the event that the plug subsequently needs to be removed, easy to retrieve from the depth of the bone canal.

Still another object of the present invention is to provide a bone cement plug which is bio-compatible with the patient, and which is inexpensive to produce.

Yet another object of the present invention is to provide an insertion tool for deploying the bone cement plug at the desired depth in the bone canal and, in the event that the bone cement plug subsequently needs to be removed, an extraction tool for retrieving the bone cement plug from the depth of the bone canal.

Still another object of the present invention is to provide an improved method for closing off the distal end of a bone canal.

SUMMARY OF THE INVENTION

These and other objects of the present invention are addressed by the provision and use of a novel bone cement plug and its associated insertion and extraction tools.

The novel bone cement plug comprises a core comprising a substantially cylindrically-shaped base portion defining a threaded bore therein extending axially and distally from a proximal end of the base portion; a first leg portion depending from and extending distally from the base portion; and a second leg portion depending from and extending distally from the base portion and opposed to the first leg portion; the base portion threaded bore being adapted to receive an expander screw to wedge apart the first and second leg portions, whereby to expand the core widthwise to secure the plug in the bone canal; and the expander screw, the screw comprising a generally cylindrically-shaped body having a distal end, and a proximal end in which is disposed a threaded bore, external threads disposed on the body, and an annular flange extending outwardly from the proximal end of the body, the screw being threadedly engageable with the core threaded bore for advancement of the screw into the core for the wedging apart of the first and second legs.

Preferably, the expander screw of the novel bone cement plug is constructed so that the screw threaded bore is provided with first and second sets of threads, the first set of threads being adapted to receive a screw insertion tool, and the second set of threads being adapted to receive a screw extraction tool.

The novel insertion tool comprises a rod having, at a distal end thereof, a tip portion of reduced diameter, the tip portion including a distal-most cylindrically-shaped portion adapted to be non-threadedly received by the screw second set of threads, and a proximal-most threaded portion adapted to be threadedly received by the screw first set of threads, whereby the insertion tool is adapted to advance the screw into the core.

The novel extraction tool comprises a rod having, at a distal end thereof, a tip portion of reduced diameter, the tip portion including a distal-most threaded portion adapted to be threadedly received by the screw second set of threads, and a proximal-most cylindrically-shaped portion adapted to be non-threadedly received by the screw first set of threads, whereby the extraction tool is adapted to withdraw the screw from the core.

The foregoing apparatus is intended to be used as follows, but does not exclude other methods of use obvious to those skilled in the art. In one method of use, three cores (small, medium and large) are sterilely packaged with the insertion tool and expander screw, with the expander screw loaded onto the medium sized core. Each core size covers a range of different bone canal sizes. The three cores together cover the whole range of bone canal sizes expected to be encountered by the surgeon in a particular surgical case. The medium sized core is generally adequate for the majority of bone canals. Also included in the sterile package is a canal sizer consisting of a smaller (e.g., 12 mm) ball on one end of a rod and a larger (e.g., 16 mm) ball on the other end of the rod. One of the balls can be unscrewed from the rod, exposing a tip designed to fit the expander screw as an extraction tool.

After preparing the bone canal in the standard fashion, the canal is sized with the canal sizer to determine to what size range the bone canal belongs. Most surgeons who are familiar with joint replacements will initially have a rough idea as to the size of the canal. If the canal is expected to be in the range of the smaller size, the surgeon first attempts to insert the smaller ball into the canal to the desired depth. If the surgeon is unable to insert the smaller ball to the desired depth, the surgeon will have to use the small sized core. If the smaller ball can be inserted to the desired depth and is reasonably spaced from the wall of the bone canal, then the medium sized core should be adequate. Similarly, for a larger canal, if the larger ball can be inserted to the desired depth, then a large sized core must be used. At any rate, with the initial rough idea as to the size range of the canal, the surgeon generally only has to size the canal once to determine the size of the core which is to be used.

After selecting the proper core, the plug is inserted into the bone canal to the desired depth, and the handle of the insertion tool is rotated to advance the expander screw. This causes the core of the plug to expand and thus increase the fixation of the plug against the wall of the bone canal.

If one should make an error in the choice of the size of the plug (with the result that it is either too loose or is unable to be inserted to the desired depth), the plug can be extracted from the canal in the following fashion. If the plug is not tightly fixated against the wall of the bone canal, the plug can be pulled out of the canal by simply withdrawing the insertion tool. If the core of the plug is expanded and is tightly jammed against the wall of the canal, the extraction tool can be used to back out the expander screw so as to allow the core of the plug to collapse. This is done by unscrewing one of the balls on the sizer tool. This exposes the extractor tip. The extractor tip is then inserted into the expander screw and rotated counter-clockwise to engage the expander screw. When the expander screw is fully engaged, the surgeon continues to rotate the extractor tip counter-clockwise so as to partially back out the expander screw. This allows the core to collapse and the plug can then be easily extracted from the canal.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 11 is a sectional view of the bone cement plug's expander screw;

FIG. 12 is a side elevational view of the distal end of an insertion tool formed in accordance with the present invention;

FIG. 13 is a side view of the distal end of an extraction tool formed in accordance with the present invention;

FIG. 41 shows the proximal end of an alternative form of insertion tool;

FIGS. 42A, 42B and 42C collectively show the bone cement plug of FIGS. 35–40 mating with a corresponding insertion tool;

FIGS. 56A, 56B and 56C collectively show the bone cement plug of FIGS. 50–55 mating with a corresponding insertion tool;

FIG. 64A is an interrupted side elevational view of an insertion tool for use with the bone cement plug of FIG. 57;

FIG. 64B is a distal end view of the insertion tool of FIG. 64A;

FIG. 65A is an interrupted side elevational view of a sleeve of the insertion tool of FIG. 64A;

FIG. 65B is a distal end view of the sleeve shown in FIG. 65A;

FIG. 66 is an enlarged side elevational view of a distal portion of the sleeve of FIG. 65A;

FIG. 67 is an end view of the distal portion of the sleeve of FIG. 66;

FIG. 68 is an interrupted side elevational view of a rod portion of the insertion tool of FIG. 64A;

FIG. 69 is an enlarged side elevational view of a portion of the rod of FIG. 68;

FIG. 70 is a side elevational view of the rod portion of FIG. 69 disposed in a distal end of the sleeve of the insertion tool of FIG. 66;

FIG. 71 is a side elevational view of the bone cement plug of FIG. 57, shown in an expanded condition;

FIG. 72 is a sectional, partly elevational, view of the bone cement plug of FIG. 58, shown in an expanded condition;

FIG. 102 is a side elevational view of still another form of bone cement plug;

FIG. 103 is a partially sectional view of the bone cement plug of FIG. 102;

FIG. 104 is similar to FIG. 102, but showing the bone cement plug in an expanded condition; and FIG. 105 is similar to FIG. 103, but showing the bone cement plug in an expanded condition.

DETAILED DESCRIPTION OF THE PREFERRED EMBODIMENTS

Figure 1:
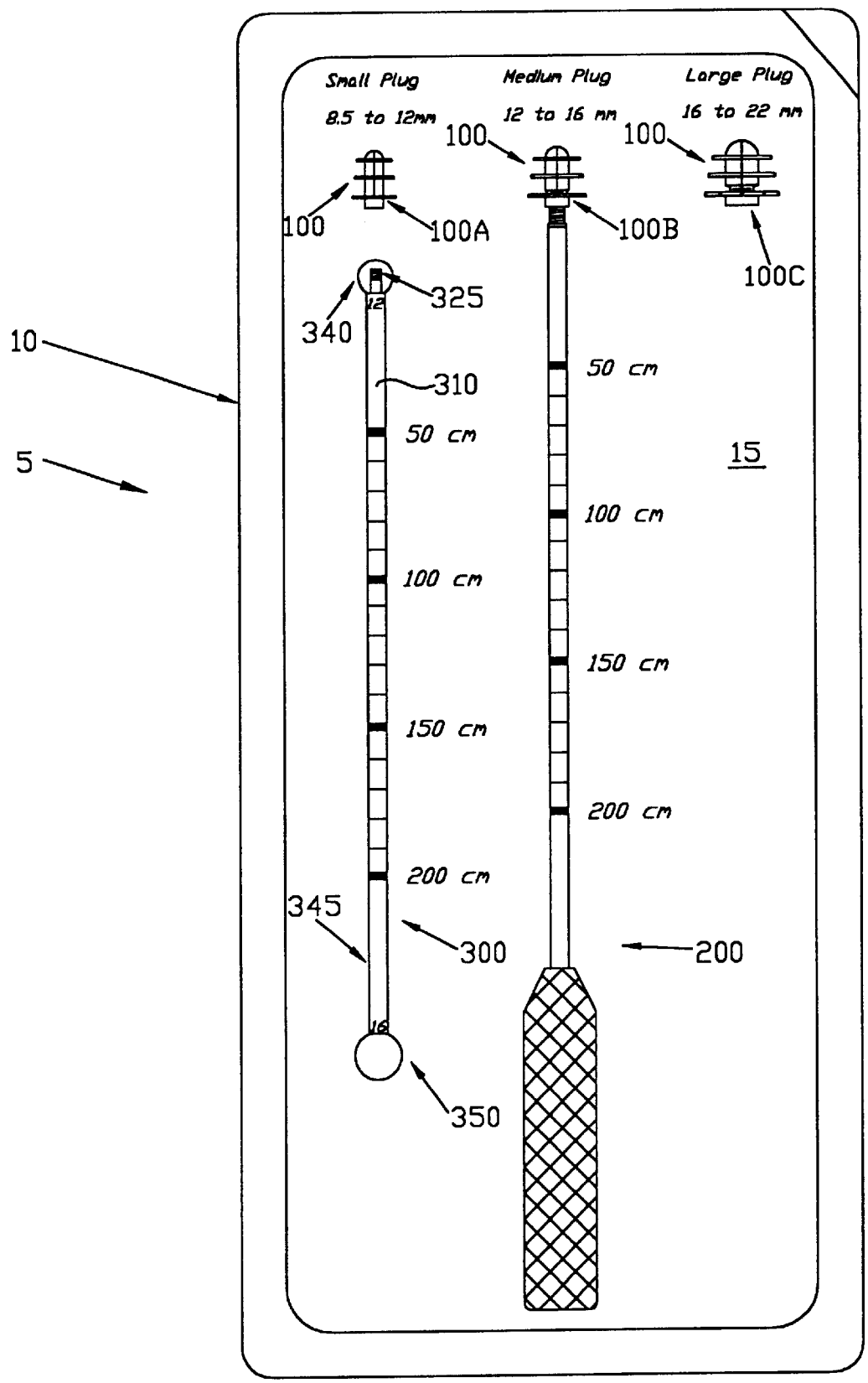
FIG. 1 is a top plan view of a bone cement plug kit formed in accordance with the present invention.

Looking first at FIG. 1, there is shown a bone cement plug kit 5 which comprises a preferred embodiment of the present invention.

Bone cement plug kit 5 generally comprises a tray 10 holding a plurality of bone cement plugs 100, an insertion tool 200 and an extraction tool 300. Preferably, tray 10 is filled with its constituent components 100, 200 and 300 at the time of manufacture, and then the tray is sealed with a transparent top tear sheet 15 so as to form a pre-packaged kit which may thereafter be opened at the time of use. As is well known in the art, tray 10 and its constituent components 100, 200 and 300 may be sterilized either before or after the package is sealed with top tear sheet 15.

Bone cement plugs 100 are shown in greater detail in FIGS. 2–7. Each bone cement plug 100 generally comprises a core 105 and an expander screw 110.

Each core 105 generally comprises a substantially cylindrically-shaped base portion 115 defining a threaded bore 120 (FIGS. 3 and 6) therein. Threaded bore 120 extends axially and distally from a proximal end surface 125 of base portion 115. A first leg portion 130 depends from, and extends distally from, base portion 115. A second leg portion 135 also depends from, and extends distally from, base portion 115. First and second leg portions 130, 135 normally sit in opposed relation to one another (FIGS. 2–4).

Figure 6:
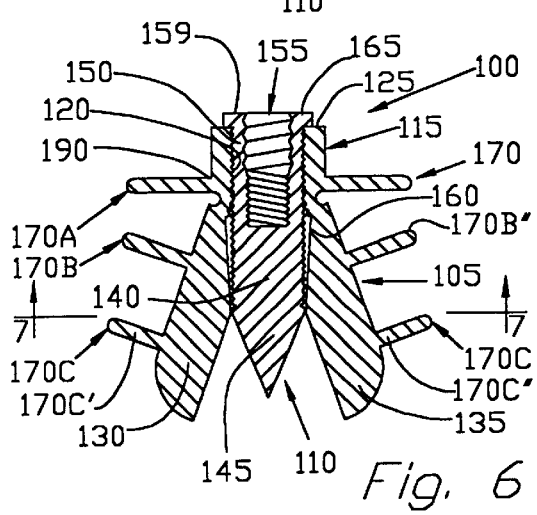
FIG. 6 is a sectional view of the bone cement plug shown in FIG. 5.
Figure 7:
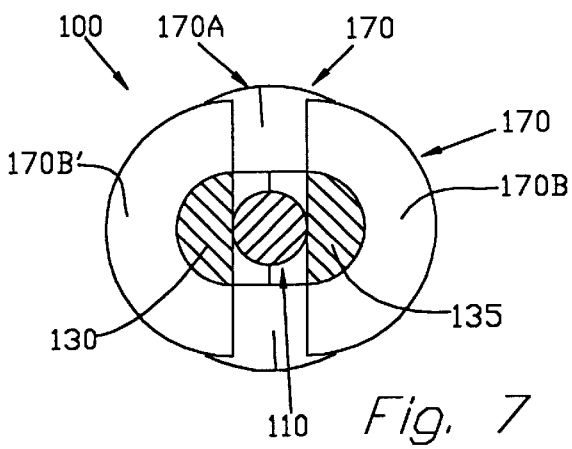
FIG. 7 is a sectional view taken along the line 7—7 of FIG. 6.

The base portion's threaded bore 120 is adapted to receive expander screw 110 so as to wedge apart the first and second leg portions 130, 135 (FIGS. 5–7), whereby to expand core 105 widthwise so as to transform the cross-sectional profile of the distal portion of bone cement plug 100 from circular (FIG. 4) to elliptical (FIG. 7). Such a transformation can be used to secure the bone cement plug in a bone canal, as will hereinafter be discussed in further detail.

Figure 5:
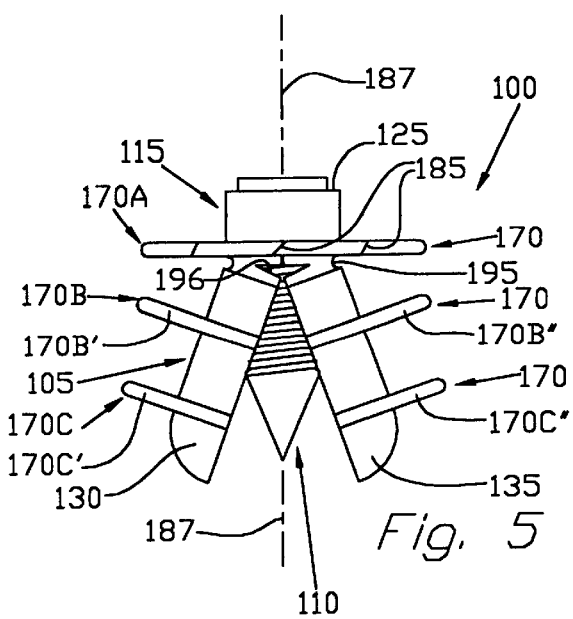
FIG. 5 is a side elevational view of the bone cement plug shown in FIG. 2, except with the plug shown in its expanded position.

To this end, expander screw 110 in turn comprises a generally cylindrically-shaped body 140 (FIGS. 3 and 6) having a tapered distal end 145 and a proximal end 150. A threaded blind hole 155 extends distally into the expander screw's body from its proximal end surface 159. External threads 160 are disposed on body 140, and an annular flange 165 extends outwardly from the proximal end of body 140. The expander screw's external threads 160 are threadedly engageable with the core's threaded bore 120, whereby clockwise rotation of expander screw 110 relative to core 105 will cause the expander screw to advance into the core so as to wedge apart the core's first and second leg portions 130, 135 (FIGS. 5–7).

Figure 2:
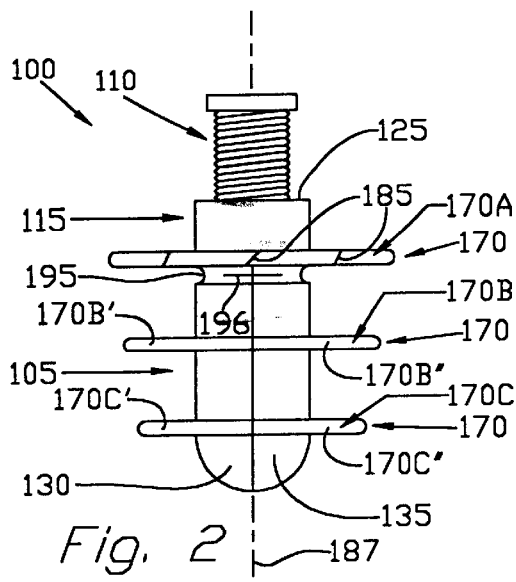
FIG. 2 is a side elevational view of a bone cement plug formed in accordance with the present invention.
Figure 3:
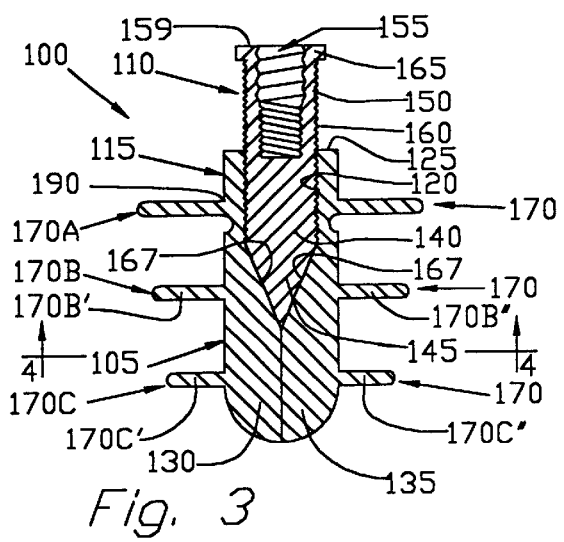
FIG. 3 is a sectional view of the bone cement plug shown in FIG. 2.
Figure 4:
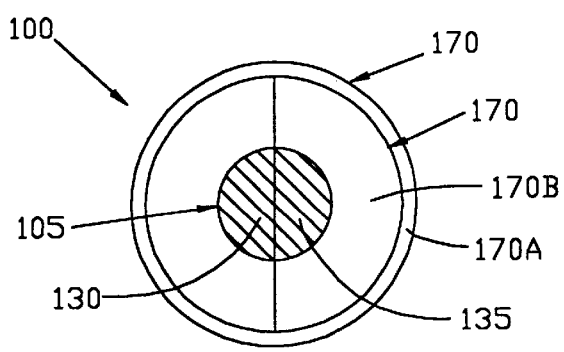
FIG. 4 is a sectional view taken along the line 4—4 of FIG. 3.

More particularly, bone cement plug 100 is arranged so that its first and second leg portions 130, 135 normally (i.e., prior to expansion) abut one another (FIGS. 2–4) and together form a substantially cylindrical configuration of substantially the same diameter as the diameter of base portion 115 (FIGS. 2 and 3). However, bone cement plug 100 is also arranged so that, after expansion, its first and second leg portions 130, 135 are separated from each other in diametrically opposed outwardly directions (FIGS. 5–7), whereby to assume a generally oval configuration in the bone canal. It will be appreciated that first and second legs portions 130, 135 cooperatively define a tapered bore portion 167 (FIG. 3) which is a co-axial extension of the core's threaded bore 120. Tapered bore portion 167 is formed so as to have a geometry which is complementary to the geometry of the expander screw's tapered distal end 145 (FIG. 3), whereby distal progress of the expander screw's tapered distal end 145 along the core's tapered bore portion 167 wedges apart the core's first and second leg portions 130, 135.

In the preferred embodiment of the invention, each bone cement plug 100 also comprises a plurality of annular flanges 170 (FIGS. 2–7) extending radially outwardly from core 105. Flanges 170 are adapted so as to be flexibly engageable with the wall of a bone canal, as will hereinafter be discussed in further detail. Preferably three flanges 170A, 170B and 170C are provided. In one form of the invention, flanges 170 have an increasing diameter as they approach the core's proximal end surface 125, and a decreasing diameter as they approach the core's distal end, such that flange 170A has a diameter greater than flange 170B, and flange 170B has a diameter greater than flange 170C, as shown in FIGS. 2 and 3.

In a preferred form of the invention, at least the proximal-most flange 170A is provided with a plurality of slits 185 (FIGS. 2, 5 and 8) which extend radially inwardly from the outer perimeter of the flange. Slits 185 extend inwardly toward an inner edge 190 (FIGS. 3, 6 and 8) where flange 170A and base portion 115 meet, but slits 185 terminate at a point spaced from the inner edge of the flange. Preferably, each of the slits 185 extends through flange 170A at an angle to the lengthwise axis 187 of bone cement plug 100, as illustrated in FIGS. 2 and 5. Typically, slits 185 extend at an angle of about 30°–60° to the lengthwise axis of bone cement plug 100. In one particular form of the invention, slits 185 extend at an angle of approximately 45° to the lengthwise axis of the bone cement plug.

Figure 9:
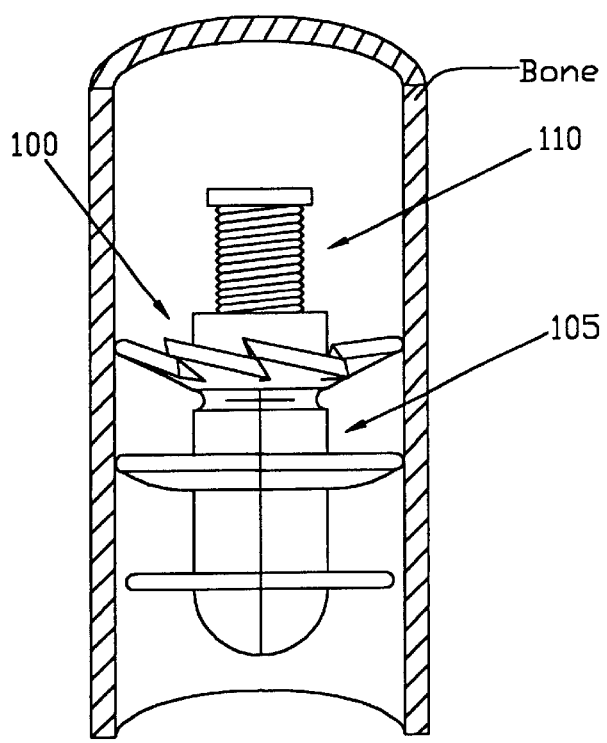
FIG. 9 is a side view, partially in section, showing the bone cement plug of FIG. 2 inserted in a bone canal.
Figure 10:
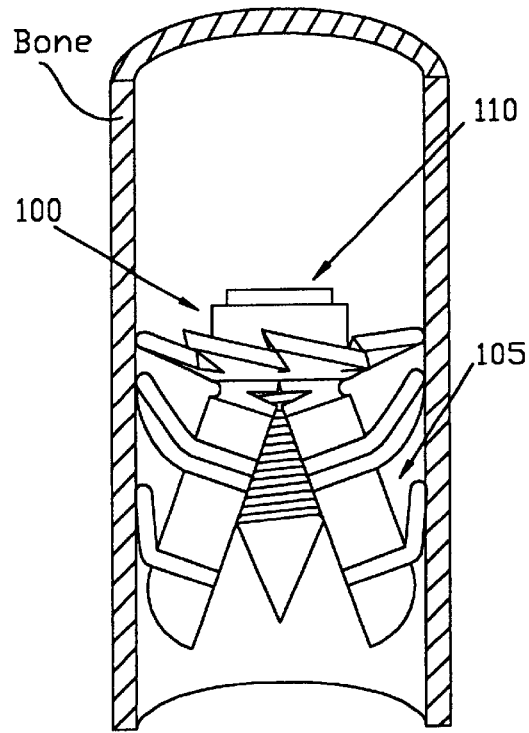
FIG. 10 is a side view, partially in section, showing the bone cement plug of FIG. 5 deployed in a bone canal.

In a preferred embodiment of the invention, the proximal-most flange 170A preferably has a diameter which exceeds the diameter of the bone canal at the location where the bone cement plug will ultimately be disposed, such that the proximal-most flange 170A will be compressed somewhat by the wall of the bone canal during deployment, as will hereinafter be discussed in further detail. In such a situation, slits 185 permit peripheral portions of the proximal-most flange 170A to override other adjacent peripheral portions of the proximal-most flange, whereby the flange can effectively size itself to the interior dimensions of the bone canal (FIGS. 9 and 10).

As noted above, slits 185 are formed in at least the proximal-most flange 170A. However, it should also be appreciated that slits 185 may be formed in one or more of the other flanges (i.e., flange 170B and/or flange 170C) if desired.

In one preferred form of the invention, the proximal-most flange 170A extends outwardly from base portion 115, and the distal-most flange 170C includes a first portion 170C' (FIGS. 2, 3, 5 and 6) which extends outwardly from first leg portion 130, and a second portion 170C" (FIGS. 2, 3, 5 and 6) which extends outwardly from second leg portion 135. Preferably, intermediate flange 170B includes a first portion 170B' which extends outwardly from first leg portion 130, and a second portion 170B" which extends outwardly from second leg portion 135.

Referring next to FIGS. 2 and 5, it will be seen that the core's base portion 115 and two leg portions 130, 135 define therebetween an annular groove 195. Preferably, annular groove 195 is disposed just distal to flange 170A. A pair of diametrically opposed, horizontally-extending slits 196 (only one of which is shown in the drawings) are positioned in annular groove 195. Slits 196 extend widthwise through the side wall of the plug and, more particularly, through proximal and substantially equal portions of the first and second legs 130, 135. Groove 195 and slits 196 together serve to facilitate outward bending of legs 130, 135 upon advancement of expander screw 110 into core 105 (FIGS. 5 and 10).

Referring next to FIG. 11, it will be seen that the expander screw's threaded bore 155 is provided with first and second sets of threads 156, 157. The second set of threads 157 is in axial alignment with the first set of threads 156; is of smaller inside diameter than the first set of threads 156; and is disposed distally to the first set of threads 156. The first set of threads 156 is adapted to receive insertion tool 200, as will be discussed in further detail below, and the second set of threads 157 is adapted to receive extraction tool 300, as will also be discussed in further detail below. It should be appreciated that (i) the first set of threads 156 is oriented in the same direction as the threads in the core's threaded bore 120, and (ii) first and second sets of threads 156, 157 have a reverse pitch from one another, as will also be discussed in further detail below.

Bone cement plugs 100 are formed out of a material which is bio-compatible. Preferably, bone cement plugs 100 are formed out of a material selected from a group of materials consisting of metal, plastic, bio-absorbable materials and metal/plastic composites. By way of example but not limitation, bone cement plugs 100 might be formed out of a plastic material, e.g., polyethylene or polypropylene. Alternatively, core 105 might be made out of a plastic material and expander screw 110 might be made out of metal. In one preferred embodiment of the invention, bone cement plug 100 is formed so that its flanges 170 are somewhat flexible, whereby they may more easily conform to the cross-sectional profile of the bone canal.

A distal portion 205 of insertion tool 200 is shown in FIG. 12. Insertion tool 200 comprises a rod 210 having, at a distal end 215 thereof, a tip portion 220 of reduced diameter. Tip portion 220 includes a distal-most, cylindrically-shaped portion 225 adapted to be non-threadedly received by the expander screw's second set of threads 157, and a proximal-most, threaded portion 230 adapted to be threadedly received by the expander screw's first set of threads 156, such that insertion tool 200 can, by rotation thereof, mate with expander screw 110 and thereafter advance screw 110 into core 105. Rod 210 is provided, at the juncture with rod tip portion 220, with an annular shoulder 235 for engagement with the expander screw's annular flange 165.

Annular shoulder 235 can be formed with a planar surface for mating with a corresponding planar surface atop the expander screw's annular flange 165. Alternatively, annular shoulder 235 may be provided with ratchet teeth 240 (FIG. 12), and expander screw 110 may be provided with complementary ratchet teeth 169 (FIG. 11), such that engagement of the rod's ratchet teeth 240 and the expander screw's counterpart ratchet teeth 169 ensures that rod 210 will begin turning expander screw 110 as the rod's annular shoulder 235 approaches the expander screw's annular flange 165. Such a construction helps prevent binding between insertion tool 200 and expander screw 110 due to any overtightening of the insertion tool relative to the expander screw. This situation can be of particular concern where the expander screw is formed of a material which is significantly softer than the material of which the rod is formed, e.g., where the rod is formed of metal and the expander screw is formed of plastic.

A distal portion 305 of extraction tool 300 is shown in FIG. 13. Extraction tool 300 comprises a rod 310 having, at a distal end 315 thereof, a tip portion 320 of reduced diameter. Tip portion 320 includes a distal-most, threaded portion 325 adapted to be threadedly received by the expander screw's second set of threads 157, and a proximal-most, cylindrically shaped portion 330 adapted to be non-threadedly received by the expander screw's first set of threads 156, such that extraction tool 300 can, by rotation thereof, withdraw screw 110 from core 105. Rod 310 is also provided, at the juncture with rod tip portion 320, with an annular shoulder 335 for engagement with screw flange 165 (or with the screw's ratchet teeth 169, if the same should be provided on screw 110).

It should be appreciated that the insertion tool's threaded portion 230 and the extraction tool's threaded portion 325 have a reverse pitch from one another, as will be discussed in further detail below. The expander screw's first set of threads 156 are engaged by the insertion tool's threaded portion 230 by turning insertion tool 200 into screw 110 in a first rotative direction (e.g., clockwise), whereupon further rotation of insertion tool 200 in that same direction will advance screw 110 into core 105 so as to expand the core.

Correspondingly, the expander screw's second set of threads 157 are engaged by the extraction tool's threaded portion 325 by turning extraction tool 300 into screw 110 in an opposite direction (e.g., counter-clockwise), whereupon further rotation of extraction tool 300 in that same opposite direction will withdraw screw 110 from core 105 so as to permit the core to return to its original, non-expanded configuration.

Returning now to FIG. 1, it will be seen that extraction tool 300 may also be used as a sizing tool by removably mounting a sizing ball 340 on threaded portion 325. If desired, a proximal end 345 of the extraction tool's rod 310 may have a second sizing ball 350 mounted thereon. By advancing a sizing ball of known diameter into the bone canal, the user may obtain an indication as to the internal diameter of the canal and, therefrom, select an appropriate size of bone cement plug for disposition within that bone canal.

By way of example, but not limitation, in the case where bone cement is to be used in a total hip replacement procedure and, more specifically, in the case where bone cement is to be injected into the intramedullary canal of the femur of an adult, the following method of use has been found to be appropriate.

Figure 14:
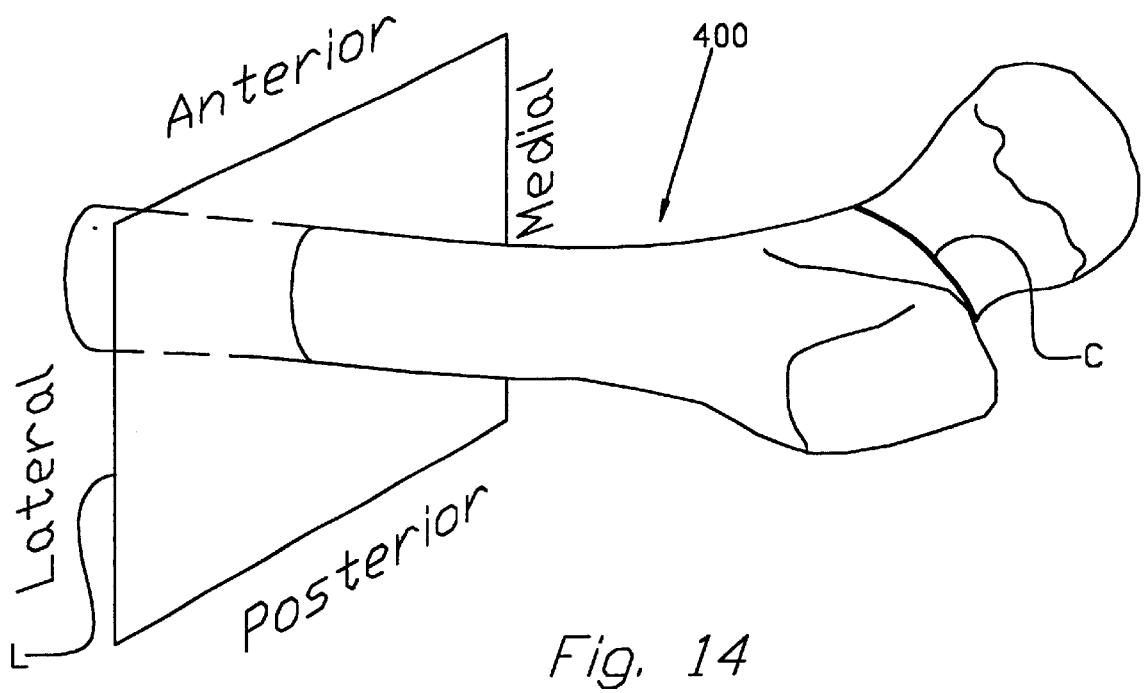
FIG. 14 is a schematic perspective view of a human femur bone.
Figure 15:
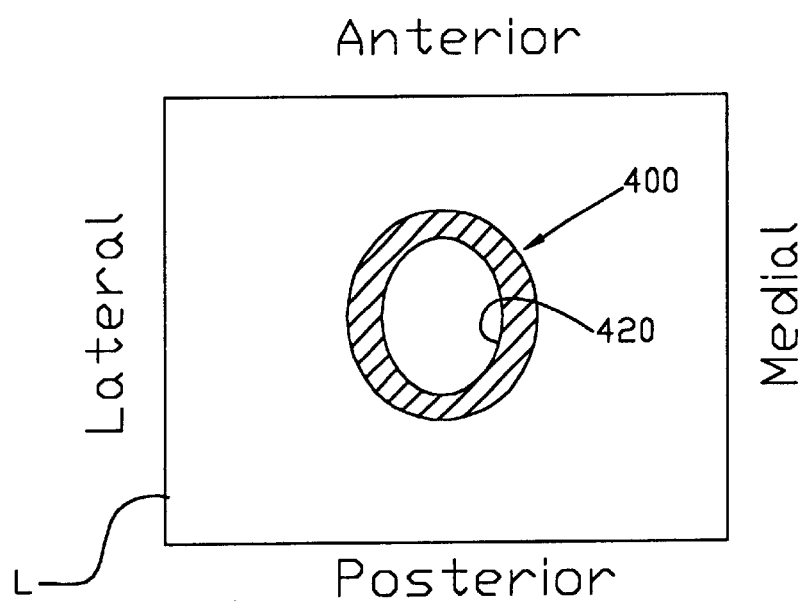
FIG. 15 is a sectional view taken through the plane L of FIG. 14.

A transverse cut C is first made through the patient's femur 400 (FIG. 14), exposing the intramedullary canal 420 (FIG. 15) which is generally oval-shaped in cross-section at the location L where bone cement plug 100 will be positioned. Canal 420 is then prepared and made ready for receipt of the bone cement and the prosthetic femoral stem (not shown) in ways well known in the art.

A bone cement plug 100 is selected by size for insertion into bone canal 420. The sizing balls 340, 350 may be used for guidance as to the approximate size plug required. Measurement markings may be placed along rod 310 of extraction tool 300 (FIG. 1) so as to help the user determine the depth of the sizing balls as they are inserted into the bone canal. A bone cement plug 100 of the type shown in FIGS. 2 and 3 is then assembled, if not previously assembled, so as to join expander screw 110 and core 105. Preferably, however, a bone cement plug 100 is provided already assembled, as shown in the bone cement plug kit 5 depicted in FIG. 1. Preferably, bone cement kit 5 is arranged to form a plurality of bone cement plugs 100 of differing sizes, e.g., plugs 100A, 100B and 100C (FIG. 1). By way of example, bone cement plug 100A might be sized to accommodate bone canals having a diameter (along the short axis) of between 8.5 mm and 12 mm, bone cement plug 100B might be sized so as to accommodate bone canals having a diameter (along the short axis) of between 12 mm and 16 mm, and bone cement plug 100C might be sized so as to accommodate bone canals having a diameter (along the short axis) of between 16 mm and 22 mm. If desired, bone cement kit 5 may comprise one bone cement plug already assembled (e.g., the bone cement plug 100B in FIG. 1), and two additional bone cement plugs (e.g., the two bone cement plugs 100A and 100C in FIG. 1) which are assembled, in the event they are needed, by combining their respective cores with the expander screw 110 from bone cement plug 100B.

Figure 16:
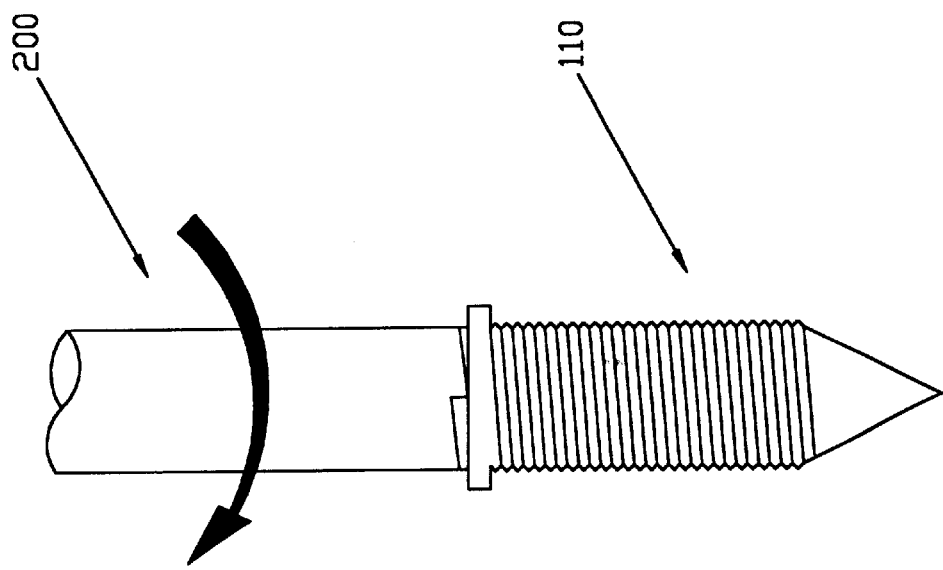
FIGS. 16 and 17 are side elevational views showing the distal end of the insertion tool engaging the bone cement plug's expander screw.
Figure 17:
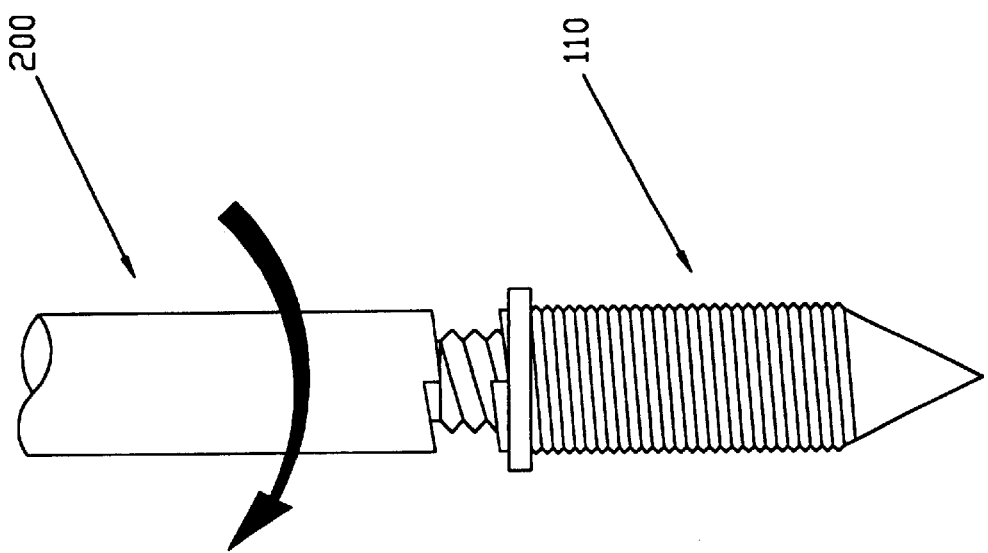

Insertion tool 200 is then screwed into the expander screw's threaded bore 155, the threaded portion 230 (FIG. 12) of insertion tool 200 threadedly engaging the first set of threads 156 (FIG. 11) of screw bore 155. The insertion tool's rod 210 is turned (FIG. 16) so as to advance the rod into screw 110 until the insertion tool's shoulder 235 (FIG. 12) engages the expander screw's flange 165 (FIG. 11) or, if ratchet teeth are provided, until the insertion tool's ratchet teeth 240 (FIG. 12) engage the screw's ratchet teeth 169 (FIG. 11), in the manner shown in FIG. 17.

Figure 8:
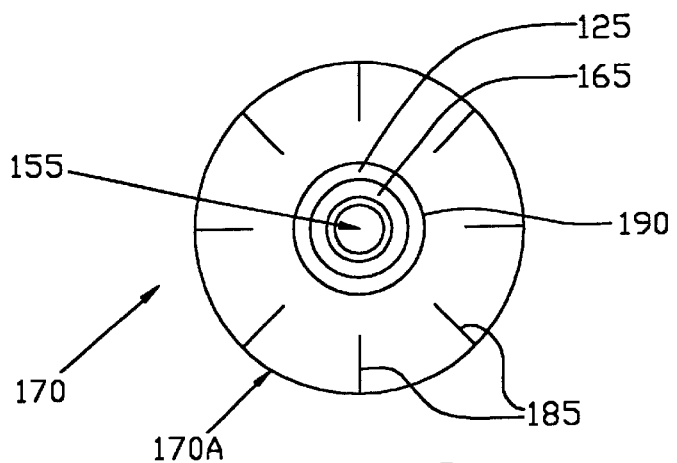
FIG. 8 is a top plan view of the bone cement plug shown in FIG. 2.
Figure 18:
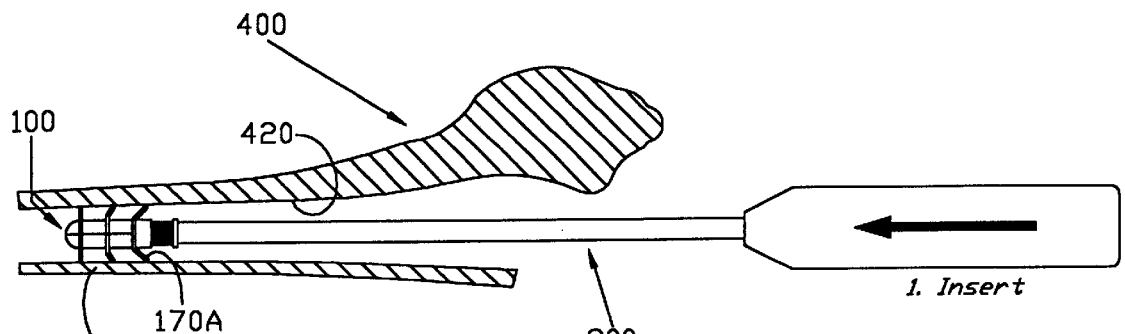
FIGS. 18–20 are schematic side views, partially in section, showing one method of deploying the bone cement plug within a bone canal.

Using insertion tool 200, bone cement plug 100 then is forced into bone canal 420 of femur 400 and moved axially into a selected position within canal 420 (FIG. 18). Measurement markings may be placed along the shaft of insertion tool 200 (FIG. 1) so as to help the user properly locate the bone cement plug at the proper depth along the bone canal. Flange 170A, being compressed by a canal wall 425, is deformed (FIG. 18). If flange 170A is provided with slits 185, as shown in FIG. 8, flange 170A generally assumes the configuration depicted in FIG. 9, wherein portions of flange 170A override other portions thereof.

Figure 19:
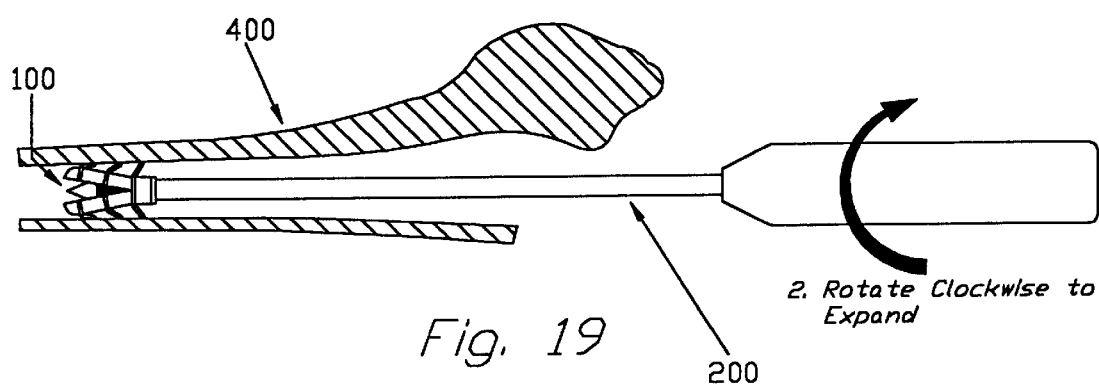
Figure 20:
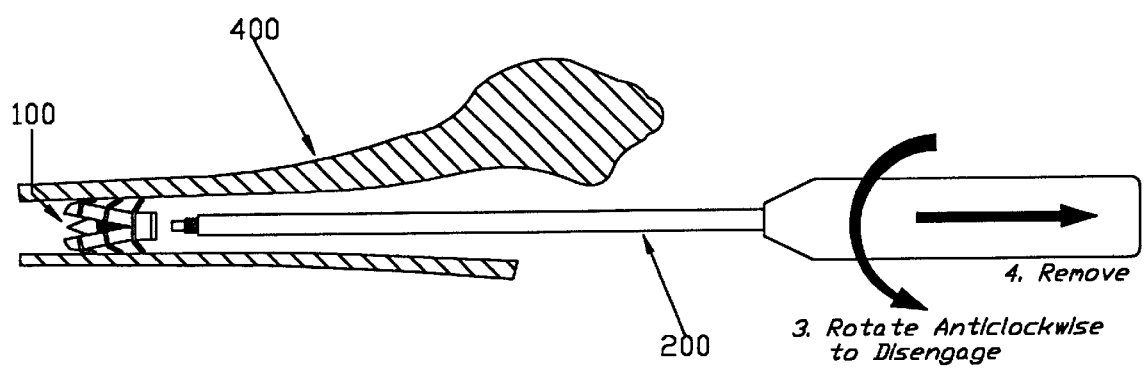

By proper rotation of insertion tool 200 (e.g., clockwise), expander screw 110 is then advanced in core 105 so as to cause expansion of core 105, such that all of the flanges 170 thereof are engaged with, and deformed against, canal wall 425, as shown in FIG. 19. This will generally secure the bone cement plug within bone canal 420. Insertion tool 200 is then rotated in the opposite direction (e.g., counter-clockwise) so as to disengage insertion tool 200 from expander screw 110 and, hence, from cement plug 100 (FIG. 20). Insertion tool 200 may then be removed from bone canal 420, leaving bone cement plug 100 in place, in its expanded condition.

Figure 21:
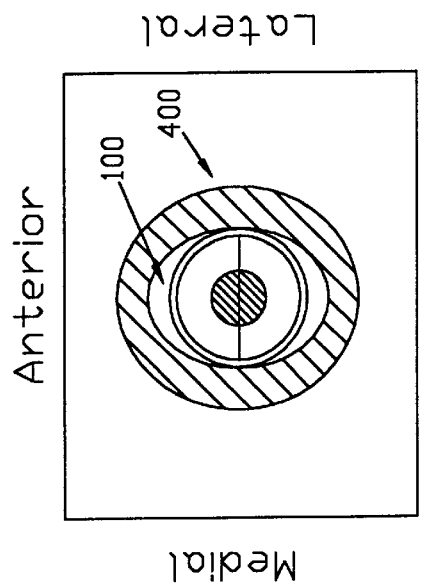
FIGS. 21 and 22 show the bone cement plug disposed in the bone canal, before the plug has been expanded by distal movement of its expander screw, with FIG. 21 looking from proximal to distal, and with FIG. 22 looking from distal to proximal, and with FIG. 22 being a sectional view taken similar to the sectional view of FIG. 4.
Figure 22:
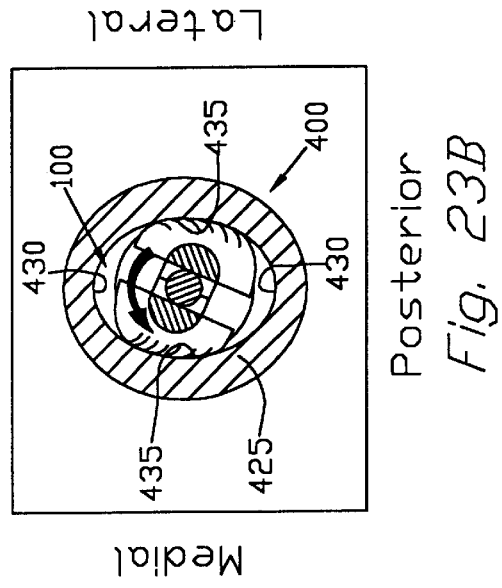
Figure 23A:
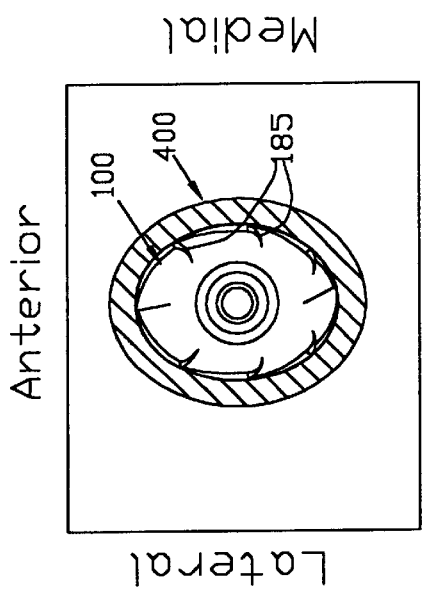
FIG. 23A shows the bone cement plug disposed in the bone canal, after the plug has been expanded by distal movement of its expander screw.
Figure 23B:
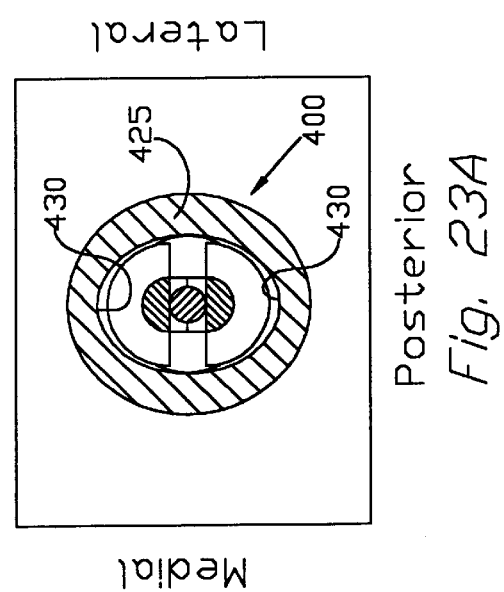
FIG. 23B shows the bone cement plug of FIG. 23A, after the entire bone cement plug has been rotated within the bone canal.

In FIGS. 21 and 22, there is illustrated the configuration of bone cement plug 100 in femur 400, prior to expansion. In FIG. 23A, it will be seen that as bone cement plug 100 expands, it becomes generally oval-shaped so as to substantially conform to the oval cross-section of femur 400. The flanges 170 move oppositely to engage opposite portions 430 of canal wall 425, which are the farthest spaced-apart wall portions. If, for some reason, after expansion, there is not an adequate jamming of bone cement plug 100 in canal 420, the expanded plug 100 may be turned within canal 420, by use of insertion tool 200, such that the extreme outward portions of flanges 170 are squeezed between opposite portions 435 of canal wall 425, which are closest together, so as to deform flanges 170 against wall portions 435, as shown in FIG. 23B.

Figure 24:
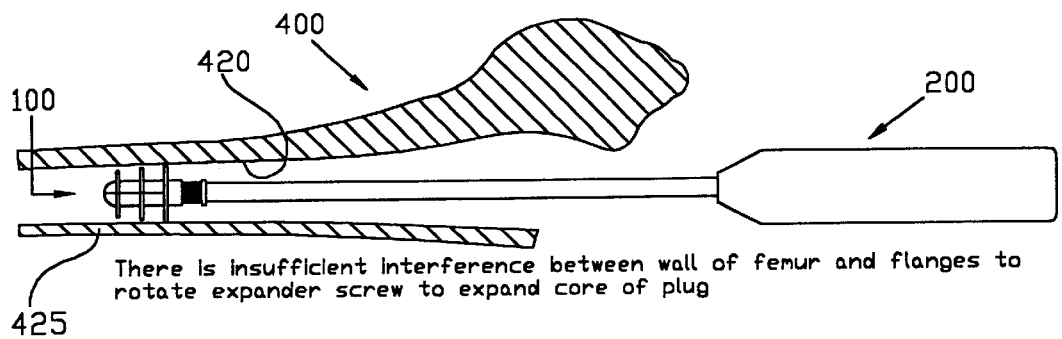
FIGS. 24–27 are schematic side views, partially in section, showing another method of deploying the bone cement plug within the bone canal.
Figure 25:
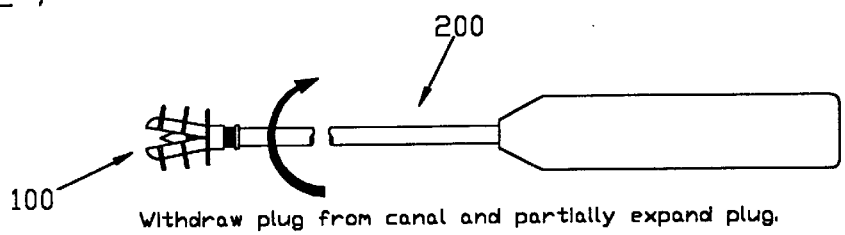
Figure 26:
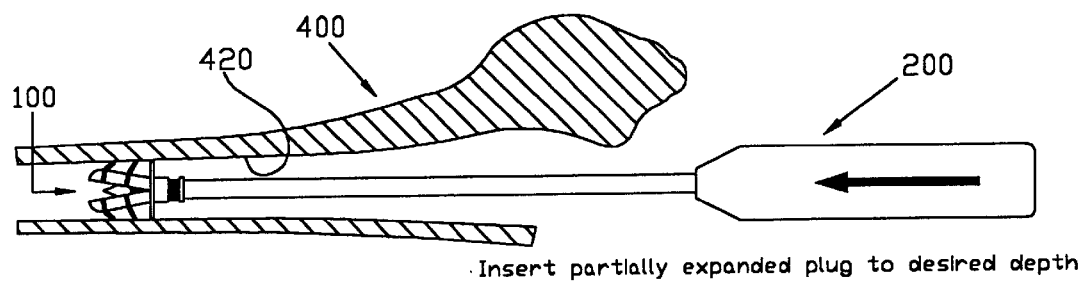
Figure 27:
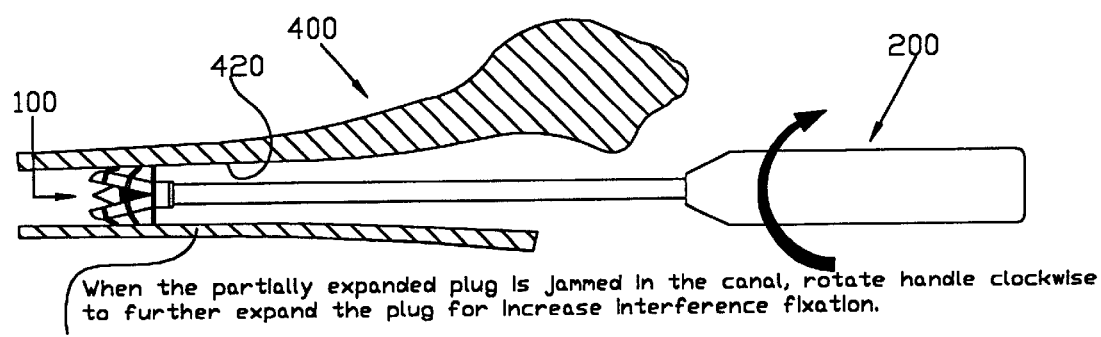

In the event that the bone cement plug 100 is introduced into bone canal 420 and is determined to only lightly engage canal wall 425 (FIG. 24), installation tool 200 may be withdrawn from canal 420, along with plug 100. Depending upon the degree of looseness experienced by plug 100 in canal 420, the plug may be replaced by a larger plug or, if the looseness is slight, the plug 100 may be slightly expanded (FIG. 25), re-introduced into canal 420 (FIG. 26), and then further expanded (FIG. 27). Again, if desired, the entire expanded plug 100 may be rotated within bone canal 420 so as to compress the long axis of the expanded plug 100 against the short axis of the bone canal (FIG. 23B).

Once bone cement plug 100 is lodged in bone canal 420, bone cement may be introduced into the canal under sufficient pressure, in ways well known in the art, to cause the cement to enter the interstices of the canal wall 425.

Figure 28:
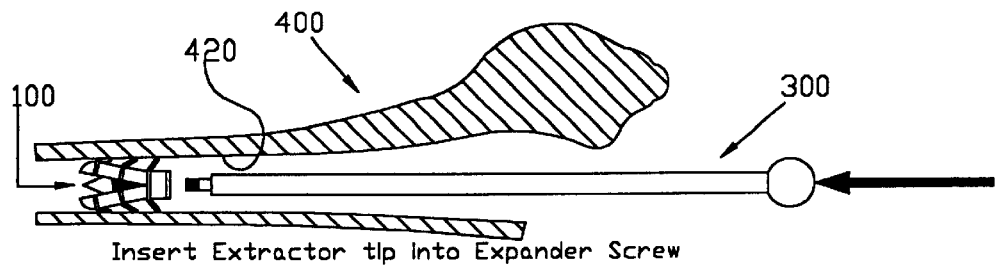
FIGS. 28–32 are schematic side views, partially in section, showing a method for retrieving the bone cement plug from the bone canal.
Figure 29:
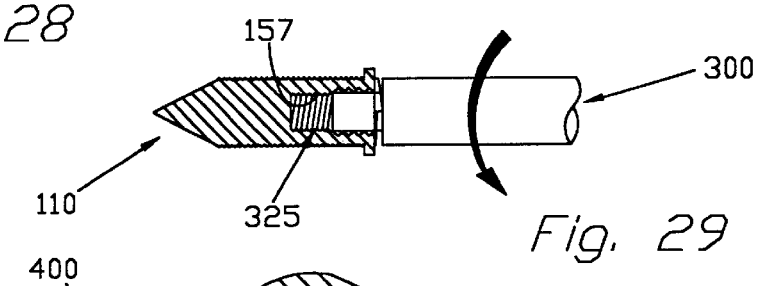
Figure 30:
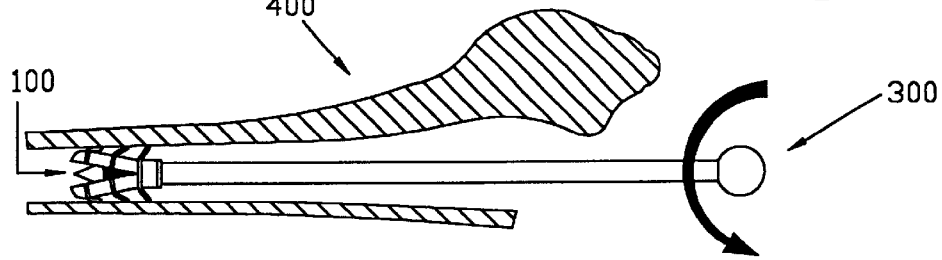
Figure 31:
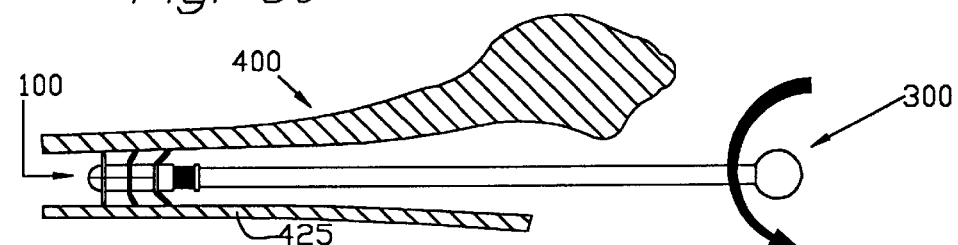
Figure 32:
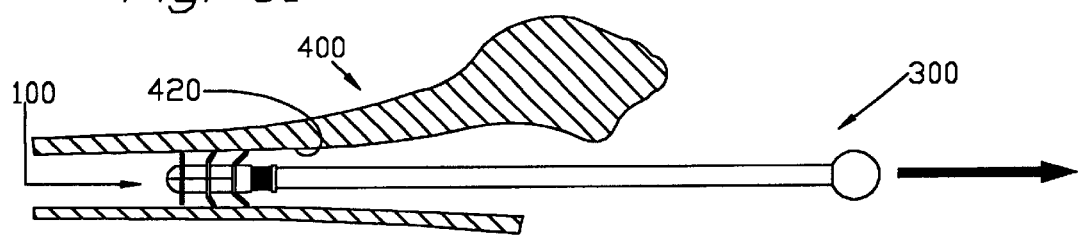

In some circumstances it may be necessary to remove a bone cement plug 100 after it has been securely deployed in bone canal 420. For example, it may be determined that the bone cement plug is insufficiently engaging the walls of the bone canal, or that the bone cement plug is too big for the bone canal, or that the plug is in the wrong position within the bone canal. To extract bone cement plug 100 from bone canal 420, extraction tool 300 is extended into canal 420 (FIG. 28) and engaged with screw 110, with the extraction tool's threaded portion 325 engaging the expander screw's second set of threads 157 (FIG. 29) with counter-clockwise rotation so as to achieve the position shown in FIG. 30. Continued counter-clockwise rotation of extraction tool 300 partially backs out expander screw 110, permitting the core's legs 130, 135 to move toward one another in response to pressure exerted thereon by canal wall 425 (FIG. 31). Thereafter, extraction tool 300 is withdrawn from the site, carrying plug 100 toward the proximal end of canal 420 (FIG. 32) and then out of the canal.

Figure 33:
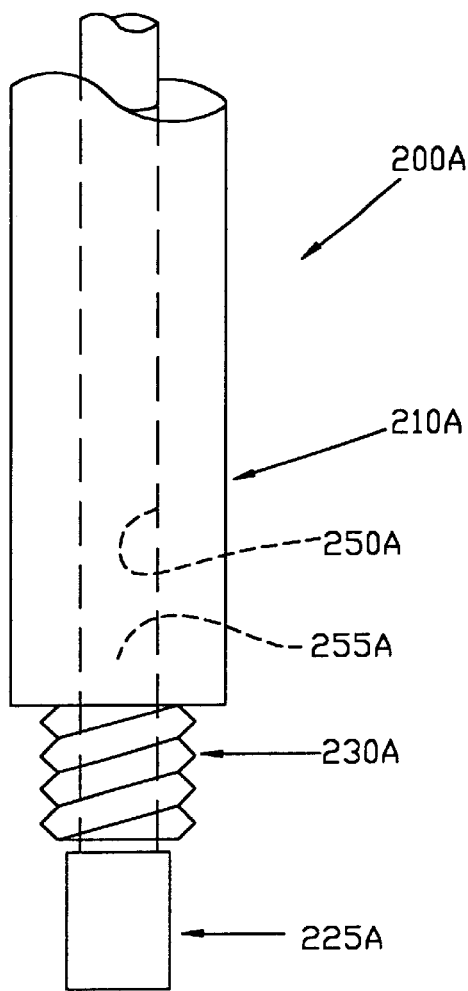
FIGS. 33 and 34 show an alternative form of insertion tool.
Figure 34:
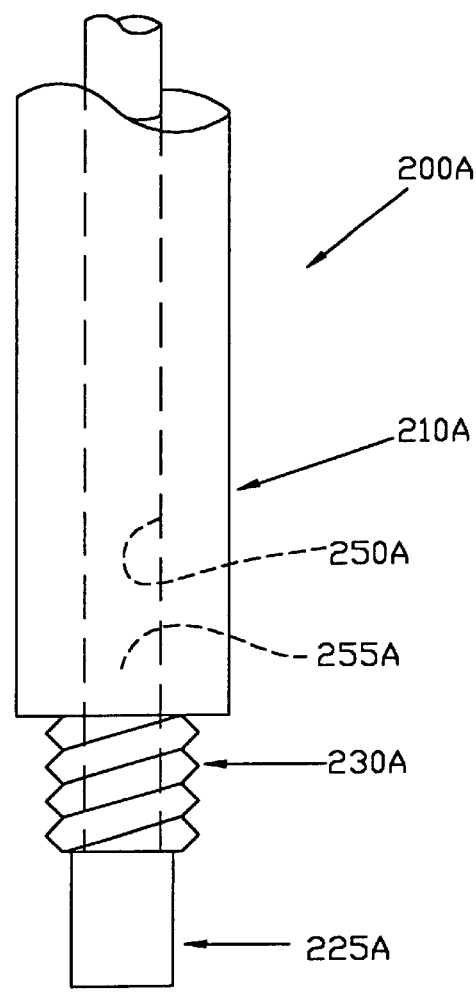
Figure 35:
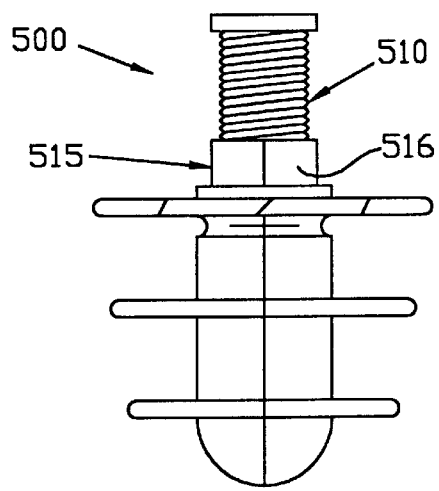
FIGS. 35–40 show an alternative form of bone cement plug.
Figure 38:
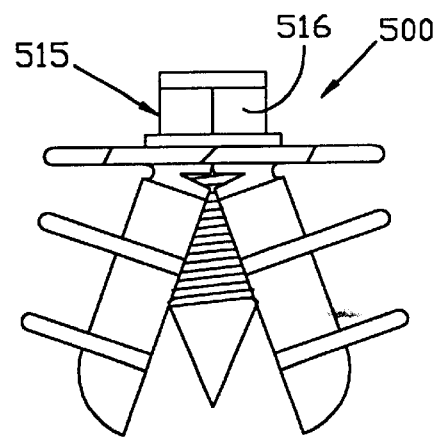
Figure 36:
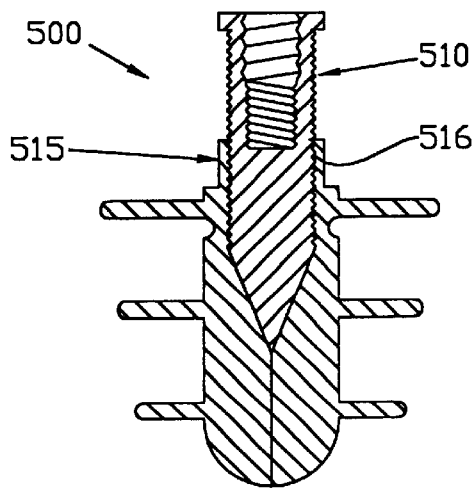
Figure 39:
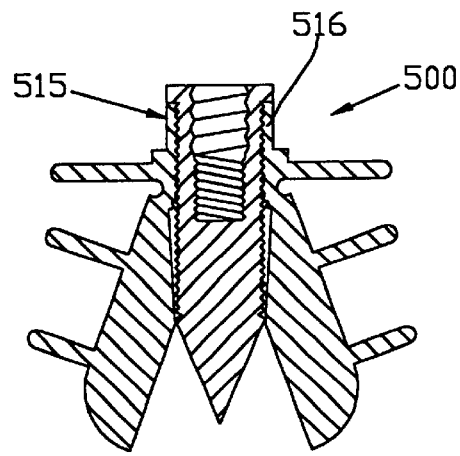
Figure 37:
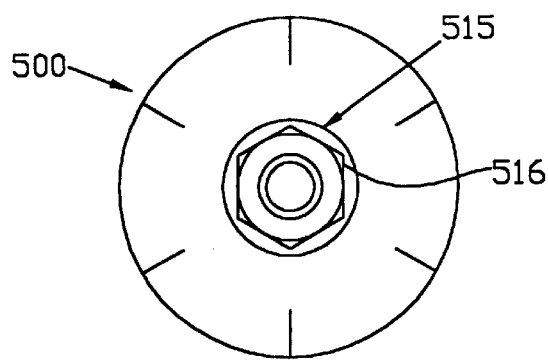
Figure 40:
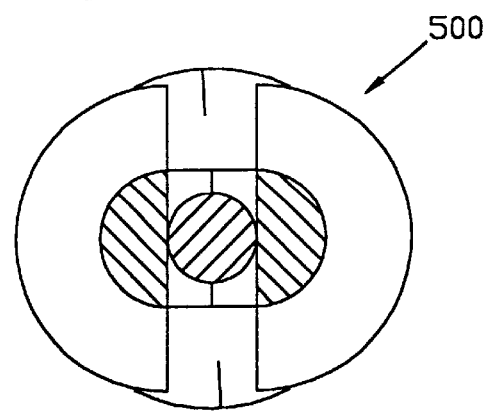
Figure 43:
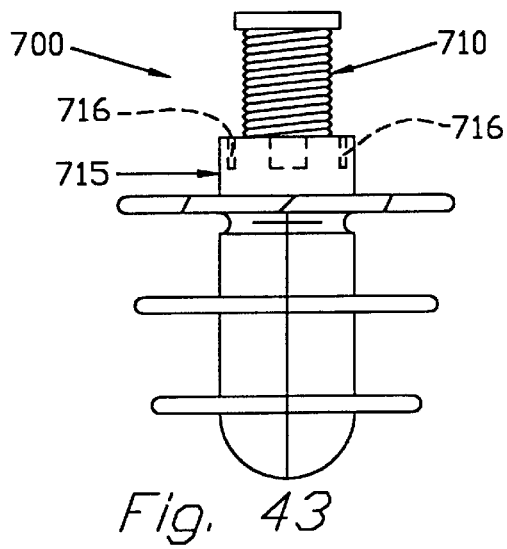
FIGS. 43–48 show another alternative form of bone cement plug.
Figure 46:
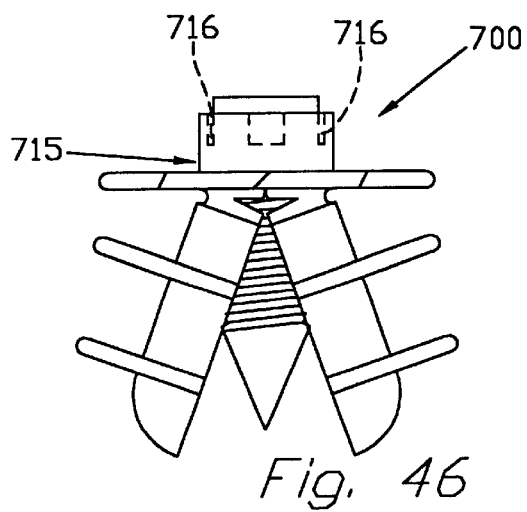
Figure 44:
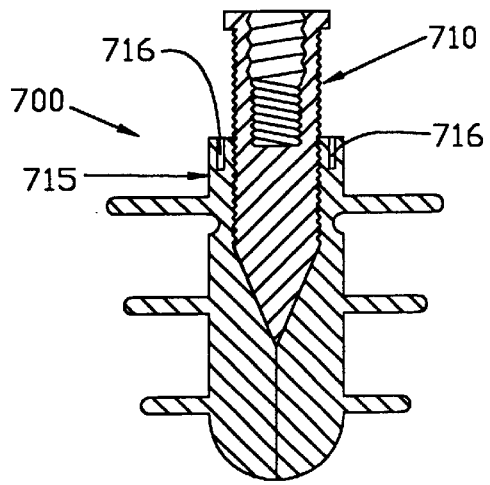
Figure 47:
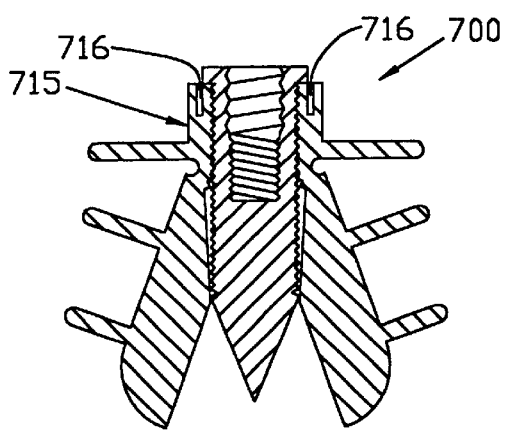
Figure 45:
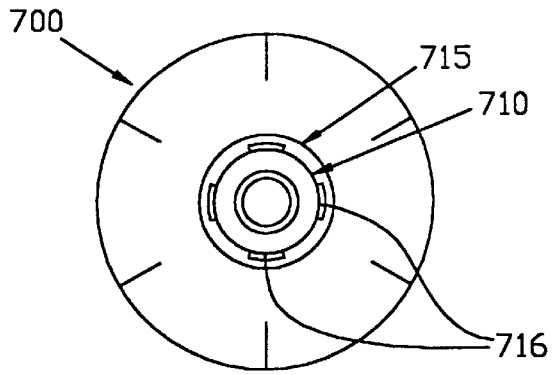
Figure 48:
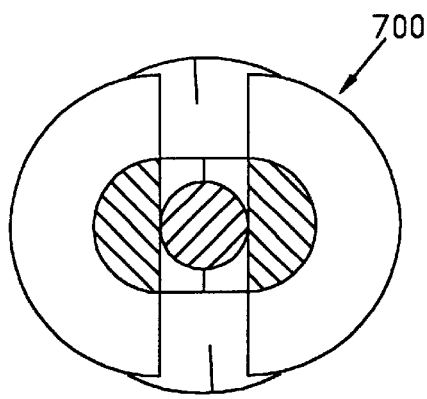

Looking next at FIGS. 33 and 34, there is shown an alternative form of insertion tool 200A. Insertion tool 200A is identical to the insertion tool 200 discussed above, except as will hereinafter be discussed. More particularly, insertion tool 200A has its rod 210A formed so that a central bore 250A is formed therein. A movable rod 255A is slidably disposed within rod 210A, and the insertion tool's distal-most, cylindrically-shaped portion 225A is attached to the distal end of movable rod 255A. As a result of this construction, the distal-most, cylindrically-shaped portion 225A may be moved towards and away from the insertion tool's threaded portion 230A.

In use, movable rod 255A is first set in its projecting position, i.e., so that the distal-most, cylindrically-shaped portion 225A is separated from the insertion tool's threaded portion 230A (FIG. 33). With insertion tool 200A in this position, the insertion tool is screwed into bone cement plug 100. As this occurs, the rod's distal-most, cylindrically-shaped portion 225A bottoms out on the bottom of the expander screw's bore 155 (FIG. 11), whereby the insertion tool is prevented from advancing too far into expander screw 110 and thereby binding the insertion tool to the expander screw. In this respect, it will also be appreciated that, to the extent that insertion tool 200A advances sufficiently far into expander screw 110 as to begin to impart some stress to the union of the expander screw threads 156 (FIG. 11) and insertion tool threads 230A (FIG. 33), the insertion tool's distal-most, cylindrically-shaped portion 230A will help take up such stress. Thereafter, when insertion tool 200A is to separate from bone cement plug 100, movable rod 255A is moved proximally within rod 210A so as to draw distal-most, cylindrically-shaped portion 225A back towards threaded portion 230A (FIG. 34). This movement releases any residual stress which may exist between the insertion tool and the bone cement plug, whereby the insertion tool may easily separate from the bone cement plug.

Looking next at FIGS. 35–40, there is shown an alternative form of bone cement plug 500. Bone cement plug 500 is identical to the bone cement plug 100 discussed above, except as will hereinafter be discussed. More particularly, bone cement plug 500 has its base portion 515 formed so that its proximal portion 516 has a hexagonal cross-section.

Bone cement plug 500 is intended to be used in conjunction with the insertion tool 600 shown in FIGS. 41 and 42A. Insertion tool 600 is identical to the insertion tool 200 discussed above, except as will hereinafter be discussed. More particularly, insertion tool 600 comprises a rod 610 which is identical to rod 210 described above. A handle 611 is fixed to the proximal end of rod 610. A sheath 612 is slidably and rotatably disposed about rod 610. Sheath 612 has a grip 613 fixed to its proximal end. The distal end of sheath 612 is arranged so as to have a hexagonal cross-section at 614 (FIG. 42A) which corresponds to the hexagonal cross-section of the proximal portion 516 of bone cement plug 500.

As a result of this construction, it will be seen that sheath 612 may be slid proximally so as to expose the distal end of rod 610. Rod 610 may then be screwed into the bone cement plug's expander screw 510, whereby rod 610 will be rotatively joined to expander screw 510. Sheath 612 may then be slid distally, using grip 613, so as to cause the sheath's hexagonal section 614 to engulf (and thereby be rotatively coupled to) the bone cement plug's hexagonally-shaped proximal portion 516. Thereafter, bone cement plug 500 and insertion tool 600 may be used in the same manner previously described with respect to bone cement plug 100 and insertion tool 200, except that the positive connection between sheath 612 and bone cement plug 500 will permit the body of the bone cement plug to be held stationary against rotation within the bone canal as expander screw 510 is advanced into the core. Additionally, the positive connection between sheath 612 and bone cement plug 500 will also permit the bone cement plug to be easily turned in an arcuate fashion by sheath 612 while bone cement plug 500 is located within the distal end of the bone canal.

Looking next at FIGS. 43–48, there is shown an alternative form of bone cement plug 700. Bone cement plug 700 is identical to the bone cement plug 100 discussed above, except as will hereinafter be discussed. More particularly, bone cement plug 700 has its base portion 715 formed so that a plurality of slots 716 are formed therein.

Figure 49:
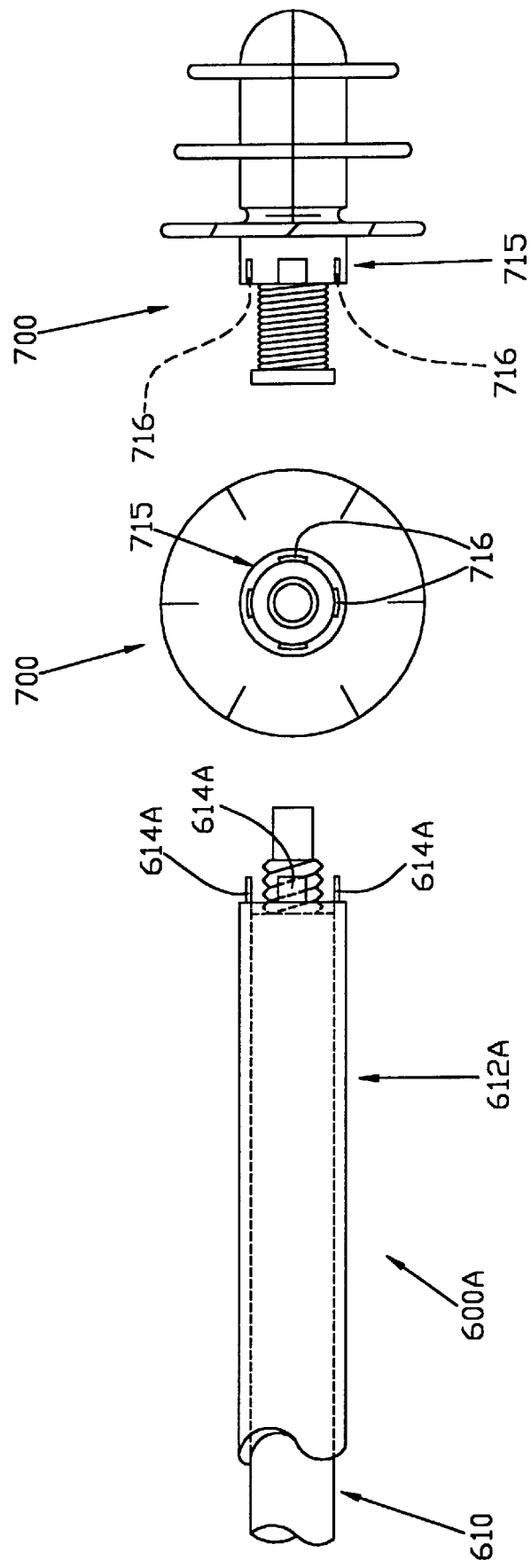
FIGS. 49A, 49B and 49C collectively show the bone cement plug of FIGS. 43–48 mating with a corresponding insertion tool.
Figure 50:
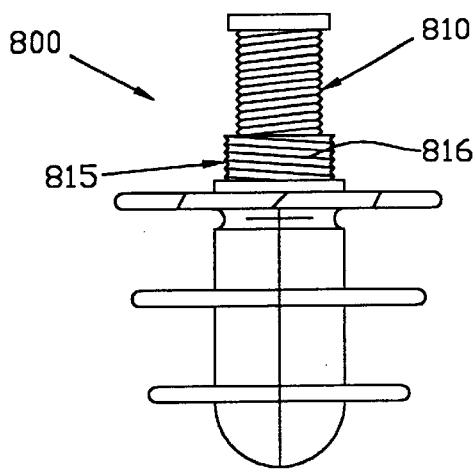
FIGS. 50–55 show still another alternative form of bone cement plug.
Figure 53:
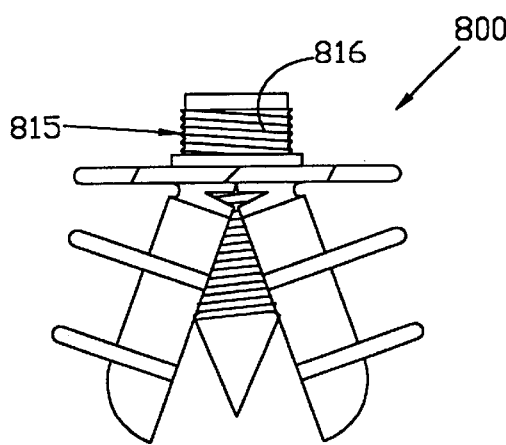
Figure 51:
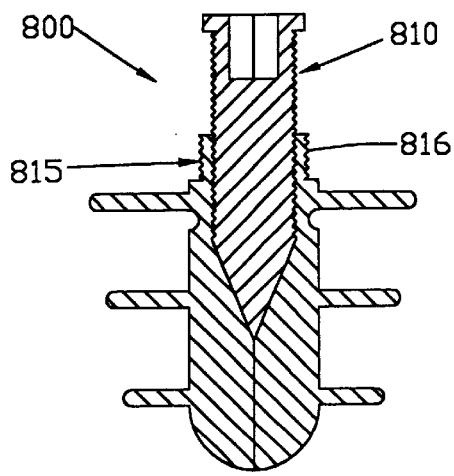
Figure 54:
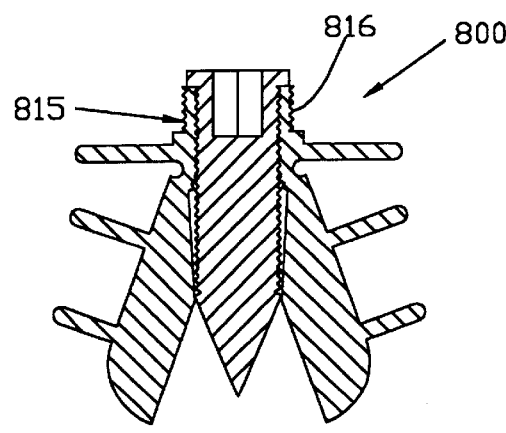
Figure 52:
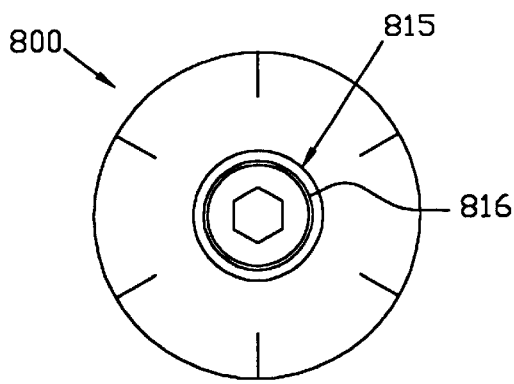
Figure 55:
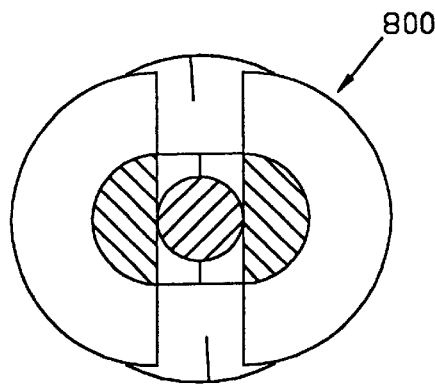

Bone cement plug 700 is intended to be used in conjunction with the insertion tool 600A shown in FIG. 49A. Insertion tool 600A is identical to the insertion tool 600 discussed above, except as will hereinafter be discussed. More particularly, insertion tool 600A comprises a sheath 612A which is slidably and rotatably disposed about rod 610. Sheath 612A has a grip (not shown in FIG. 49A but preferably identical to the grip 613 shown in FIG. 41) fixed to its proximal end. The distal end of sheath 612A is arranged so as to have a plurality of projections 614A which correspond to the slots 716 formed in the proximal portion 715 of bone cement plug 700.

As a result of this construction, it will be seen that sheath 612A may be slid proximally so as to expose the distal end of rod 610. Rod 610 may then be screwed into the bone cement plug's expander screw 710, whereby rod 610 will be rotatively joined to expander screw 710. Sheath 612A may then be slid distally, using its aforementioned grip, so as to cause the sheath's projections 614A to engage, and thereby to be rotatively coupled to, the bone cement plug's slots 716. Thereafter, bone cement plug 700 and insertion tool 600A may be used in the same manner previously described with respect to bone cement plug 100 and insertion tool 200, except that the positive connection between sheath 612A and bone cement plug 700 will permit the body of the bone cement plug to be held stationary against rotation within the bone canal as expander screw 710 is advanced into the core. Additionally, the positive connection between sheath 612A and bone cement plug 700 will also permit the bone cement plug to be easily turned in an arcuate fashion by sheath 612A while bone cement plug 700 is located within the distal end of the bone canal.

Looking next at FIGS. 50–55, there is shown an alternative form of bone cement plug 800. Bone cement plug 800 is identical to the bone cement plug 100 discussed above, except as will hereinafter be discussed. More particularly, bone cement plug 800 has its base portion 815 formed so that a set of screw threads 816 are formed thereon. The set of screw threads 816 is oriented in the opposite direction relative to the expander screw's external screw threads 160 (FIG. 3).

Bone cement plug 800 is intended to be used in conjunction with the insertion tool 600B shown in FIG. 56A.

Insertion tool 600B is identical to the insertion tool 600 discussed above, except as will hereinafter be discussed. More particularly, insertion tool 600B comprises a sheath 612B which is slidably and rotatably disposed about rod 610. Sheath 612B has a grip (not shown in FIG. 56A but preferably identical to the grip 613 shown in FIG. 41) fixed to its proximal end. The distal end of sheath 612B is arranged so as to have a set of screw threads 614B which corresponds to the set of screw threads 816 which are formed on the proximal portion 815 of bone cement plug 800.

As a result of this construction, it will be seen that sheath 612B may be slid proximally so as to expose the distal end of rod 610. Rod 610 may then be screwed into the bone cement plug's expander screw 810, whereby rod 610 will be rotatively joined to expander screw 810. Sheath 612B may then be slid distally and rotated, using its aforementioned grip, so as to cause the sheath's set of screw threads 614B to engage, and thereby to be rotatively coupled to, the bone cement plug's set of screw threads 816. Thereafter, bone cement plug 800 and insertion tool 600B may be used in the same manner previously described with respect to bone cement plug 100 and insertion tool 200, except that the positive connection between sheath 612B and bone cement plug 800 will permit the body of the bone cement plug to be held stationary against rotation within the bone canal as expander screw 810 is advanced into the core. Additionally, the positive connection between sheath 612B and bone cement plug 800 will also permit the bone cement plug to be easily turned in an arcuate fashion by sheath 612B while bone cement plug 800 is located within the distal end of the bone canal.

Referring next to FIGS. 57–63, 71 and 72, it will be seen that an alternative embodiment of bone cement plug 900 includes a core 905 and an expander member 910, such as a screw. The core 905 includes a substantially cylindrically-shaped base portion 915 defining a bore 920 having internal teeth 922 formed therein.

Figure 61:
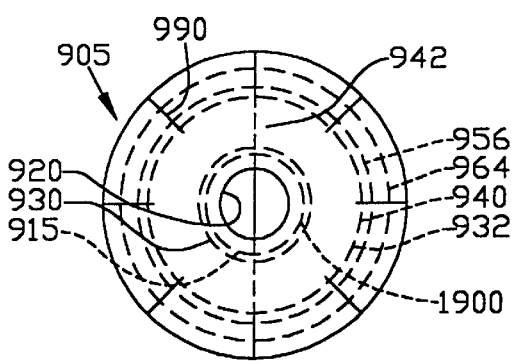
FIG. 61 is a top plan view of the core portion of FIG. 59.

A first leg portion 930 of plug 900 depends from, and extends distally from, base portion 915. A first protrusion 932, at a distal end 934 of first leg portion 930, extends outwardly from an outside wall 936 of the first leg portion through an arc of about 180° (FIG. 61).

Similarly, a second leg portion 935 depends from, and extends distally from, base portion 915. A second protrusion 937 at a distal end 938 of second leg portion 935 extends outwardly from an outside wall 939 of the second leg portion through an arc of about 180°, and oppositely to the arc of the first protrusion 932. Thus, the arcs through which the first and second protrusions 932, 937 extend are such that, prior to expansion, the first and second protrusions 932, 937 form a planar circular distal flange 940.

The base portion toothed bore 920 is adapted to receive the screw, or other expander member, 910 so as to wedge apart the first and second leg portions 930, 935, as shown in FIGS. 71 and 72, whereby to expand the core 905 widthwise in the bone canal 420.

In the embodiments described hereinabove and shown in the drawings prior to FIG. 57, the core's bore 120 terminates a substantial distance from the distal end of the core. Because of the proximally-located leg pivot point (located approximately at annular groove 195), and because of the relatively long lever arm of the first and second leg portions 130 and 135, and because of the flexibility of the leg portions 130 and 135 (which preferably are made of a plastic material), and because of the consequent deformation of the leg portions when impinging against the wall of the bone canal, the radial force which can be generated is limited.

Figure 57:
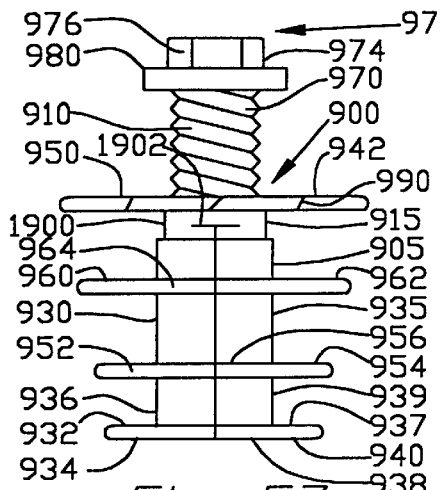
FIG. 57 is a side elevational view of an alternative form of bone cement plug.
Figure 59:
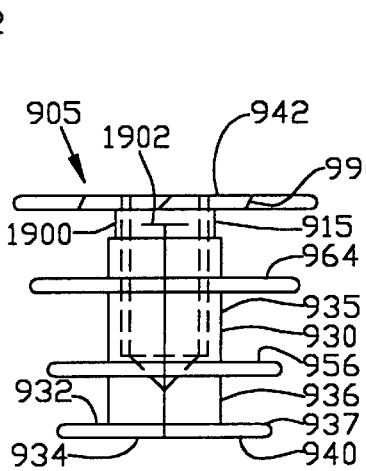
FIG. 59 is a side elevational view of a core portion of the bone cement plug of FIG. 57.

By comparison, in the embodiments of the core shown in FIG. 57 and thereafter, the core's bore terminates more distally. In these embodiments, the expander member provides more rigid support to the distal ends of the leg portions, but the leg distal ends do not spread apart as much. To compensate for the more limited spreading of the leg portions, the embodiments of plug shown in FIG. 57 and thereafter are provided with outwardly-extending protrusions at the leg distal ends.

The core 905 preferably is provided with an annular flange 942 proximate a proximal end 950 of the core, which flange 942 extends outwardly from core base portion 915, and which flange 942 is engageable with the bone canal wall 425. The flange 942 is provided with radial slits 990 similar to slits 185 disposed in proximal flange 170A shown in FIGS. 2, 5 and 8, and performing the same functions as slits 185. That is, the slits 990 permit portions of the proximal flange 942 to override other portions, when the proximal flange is expanded against the wall of the bone canal. In addition, the sharp edges provided by the slits engage the irregularly shaped wall of the bone canal and, in the case of an expander member with right-handed screw threads, resist clockwise rotation of the plug when the expander member is advanced into the core.

A further pair of opposed protrusions 952, 954 are disposed on core leg portions 930, 935, respectively, between annular flange 942 and first and second protrusions 932, 937. The further pair of opposed protrusions 952, 954, prior to expansion, together form a second annular flange 956 having a diameter equal to, or less than, the diameter of proximal annular flange 942, and a diameter equal to, or greater than, the diameter of distal flange 940.

The core 905 preferably is provided with a still further pair of opposed protrusions 960, 962 disposed between proximal annular flange 942 and the pair of opposed protrusions 952, 954. Prior to expansion, opposed protrusions 960, 962 form a third annular flange 964 having a diameter equal to, or less than, the diameter of proximal annular flange 942, and a diameter equal to, or greater than, the diameter of the second annular flange 956.

As shown in FIGS. 57–61, leg portions 930, 935, prior to expansion, abut each other and together form a substantially cylindrical configuration of substantially the same diameter as a diameter of base portion 915. After expansion (FIGS. 71 and 72), leg portions 930, 935 are separated from each other, and extend from base portion 915 in diametrically-opposed outward directions, so as to assume a generally oval configuration in the bone canal 420, similar to that illustrated in FIG. 21 with respect to a previously-described embodiment of the invention.

Figure 62:
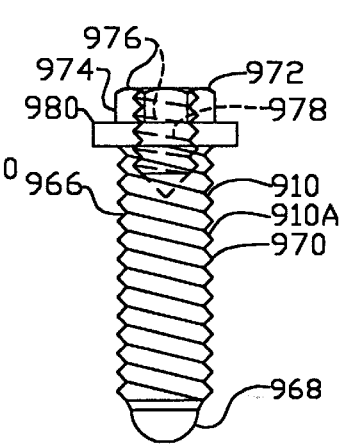
FIG. 62 is a side elevational view of an expander screw portion of the bone cement plug of FIG. 58.
Figure 58:
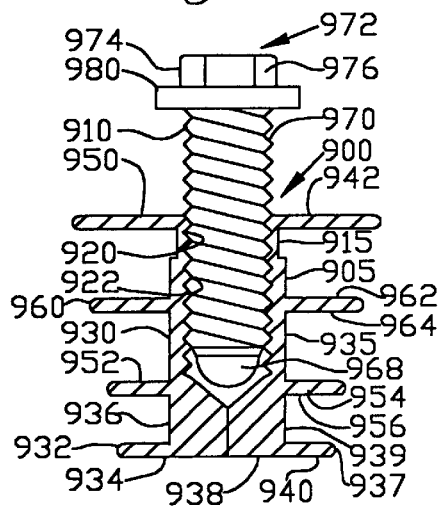
FIG. 58 is a sectional, partly elevational, view of the bone cement plug of FIG. 57.
Figure 60:
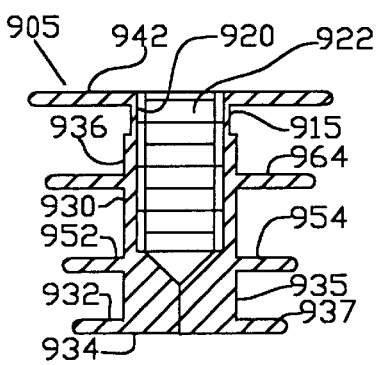
FIG. 60 is a sectional view of the core portion of FIG. 59.
Figure 63:
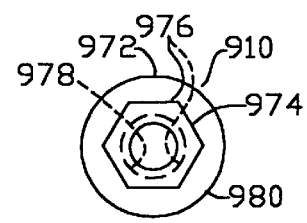
FIG. 63 is a top plan view of the expander screw of FIG. 62.

Referring now to FIGS. 62 and 63, it will be seen that the expander member 910 may be in the form of a screw 910A having a generally cylindrically-shaped body 966 and having a reduced distal end 968 which may be generally pointed, as shown and described hereinabove, or rounded, as shown in FIG. 62. The screw body 966 is provided with screw threads 970 for engagement with the core bore internal teeth 922 which, when expander member 910 comprises the screw 910A, comprise screw threads complementary to the screw threads 970 of screw 910A. At a proximal end 972 of screw 910A, there is provided a head 974 having connection means 976 for connection with an insertion tool and/or an extraction tool.

The screw connection means 976 preferably include internal screw threads 978 for receiving a threaded tool distal end portion, to be described hereinbelow, and a head configuration, such as hexagonal, and a flange 980, for engagement with a complementarily-configured second tool distal end portion.

Turning to FIGS. 64–70, it will be seen that an insertion tool 1000 includes a rod 1010 (FIGS. 64A and 68–70) having, at a distal end 1015 thereof, a tip portion 1020 provided with external threads 1030, such that rod 1010 can, by rotation thereof, mate with expander screw 910A and thereby hold the expander screw to the remainder of the insertion tool, as will be discussed in further detail below. The insertion tool 1000 further includes a sleeve 1035 (FIGS. 64–67 and 70) having a bore 1038 therethrough in which rod 1010 is rotatably mounted. The sleeve 1035 is provided with a grip portion 1040 and an elongated shank portion 1042. The rod 1010 is provided with an end cap 1044 (FIGS. 64A and 68) which is disposed proximally of end 1046 of grip portion 1040, and which is fixed to rod 1010 and enables easy turning of the rod within sleeve 1035.

The sleeve 1035 is further provided with connection means 1050 (FIG. 70) for engaging the screw body proximal end 972. The connection means 1050 may comprise a socket 1052 configured complementarily to expander screw head 974. Thus, the insertion tool 1000 is provided with connection means on the rod tip portion 1020, such as screw threads 1030, for connection to the screw connection means 976, such as internal threads 978, and is further provided with connection means 1050 on the sleeve 1035, such as socket 1052, for connection to the screw head 974. Preferably, expander screw 910A is pre-mounted on core 905 such that expander screw 910A is only partially in bore 920, without wedging first and second leg portions 930, 935 apart.

In operation, the distal end of insertion tool 1000 is brought into engagement with the expansion screw 910A. The rod external threads 1030 engage the screw internal threads 978, and the sleeve socket 1052 receives the screw head 974. The operator holds sleeve 1035 by the grip portion 1040 and turns rod 1010 by rotating end cap 1044. The sleeve socket 1052 surrounds screw head 974 and prevents turning of expander screw 910A while rod 1010 is screwed into the expander screw. This action secures expander screw 910A to sleeve 1035.

Once rod 1010 is threadedly secured to expander screw 910A, insertion tool 1000 is used to bring bone cement plug 900 to the surgical site, where it is forced into preliminary engagement with the walls of the bone canal at a desired depth. More specifically, the proximal flange 942 of bone plug 900 is buckled against the bone canal wall, the outer edges of the flange serving to jam the plug 900 in the bone canal and to prevent rotation of the plug in the bone canal. Thereafter, sleeve 1035 is turned, to turn expander screw 910A, thereby advancing the expander screw into core 905 so as to cause leg portions 930, 935 to be expanded and further locking the bone cement plug to the recipient bone by engagement of annular flanges 940, 956 and 964 with the bone canal wall. Rod 1010 is then unscrewed from the internal threads 978 of the expander screw, whereby insertion tool 1000 can be withdrawn, leaving bone cement plug 900 in the bone canal in an expanded state.

Figure 73:
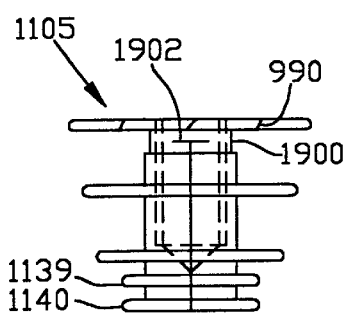
FIG. 73 is a side elevational view of a core portion of an alternative embodiment of bone cement plug.
Figure 74:
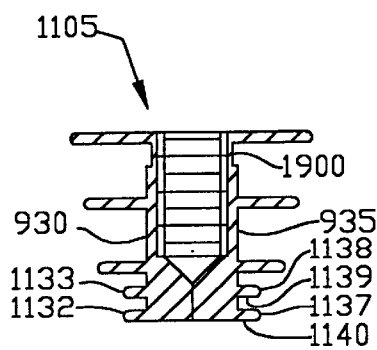
FIG. 74 is a sectional view of the core portion of FIG. 73.
Figure 75:
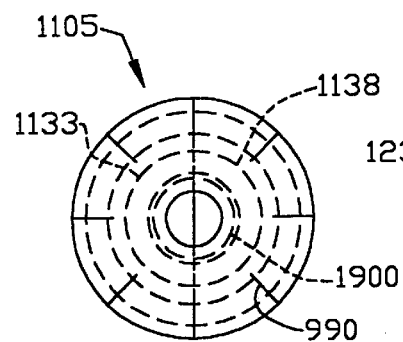
FIG. 75 is a top plan view of the core portion of FIG. 73.

In the alternative embodiment of core 1105, shown in FIGS. 73–75, the core structure is similar to the core structure shown in FIGS. 57–61, except that for the distal-most protrusions 932, 937, there is substituted a pair of protrusions 1132, 1133 on first leg portion 930, and a pair of protrusions 1137, 1138 on second leg portion 935. The protrusions 1133, 1138 form a circular flange 1139 (FIG. 74) of a diameter equal to the diameter of a flange 1140 formed by protrusions 1132, 1137. The diameter of flanges 1139 and 1140 are somewhat less than the diameter of the single distal flange 940 of the embodiment shown in FIG. 57. When the two flanges 1139, 1140 engage the bone canal wall, they are less likely to flex than is flange 940. The edges of flanges 1139 and 1140 tend to dig into the wall of the bone canal, rather than flex. This embodiment is installed similarly to, and serves the same purpose as, the previously described embodiment of FIGS. 57–61.

Figure 76:
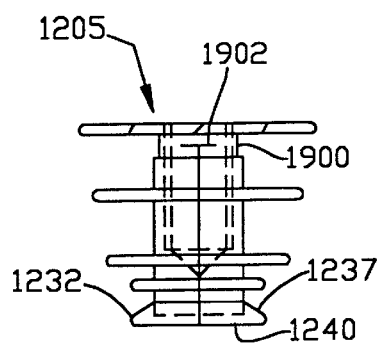
FIG. 76 is a side elevational view of a core portion of an alternative embodiment of bone cement plug.
Figure 77:
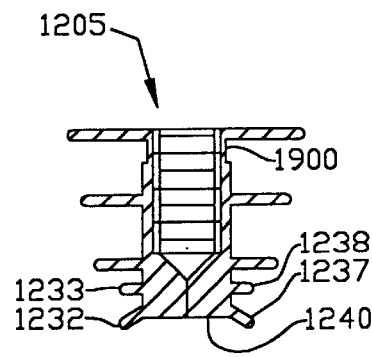
FIG. 77 is a sectional view of the core portion of FIG. 76.
Figure 78:
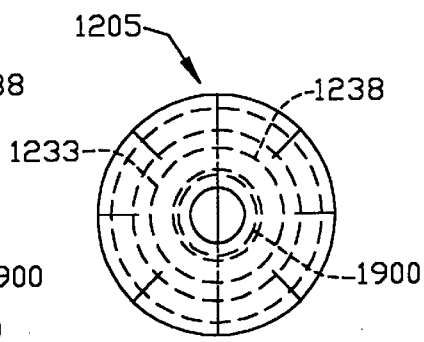
FIG. 78 is a top plan view of the core portion of FIG. 76.

In the alternative embodiment of core 1205, shown in FIGS. 76–78, the core structure is similar to the core structure shown in FIGS. 73–75, except that in this embodiment, distal-most protrusions 1232, 1237 are inclined distally to form, prior to expansion, a generally inverted saucer configuration 1240. The inverted saucer configuration of the distal flange 1240 tends to tilt proximally when the legs are spread apart, causing the distal flange edges to engage the wall of the bone canal closer to perpendicular to the core axis, or inclined distally. Such an angle of engagement of the distal flange against the bone canal wall resists distal migration of the plug. This embodiment is installed similarly to, and serves the same purpose as, the previously-described embodiments of FIGS. 57–61 and FIGS. 73–75.

Figure 79:
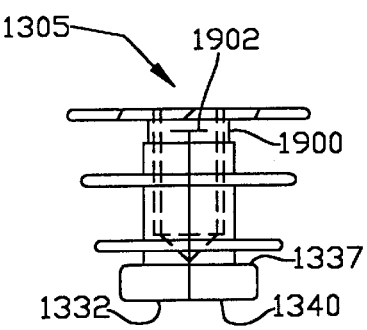
FIG. 79 is a side elevational view of a core portion of another alternative embodiment of bone cement plug.
Figure 80:
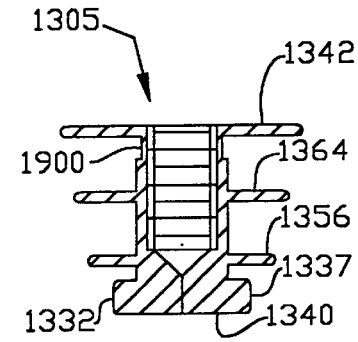
FIG. 80 is a sectional view of the core portion of FIG. 79.
Figure 81:
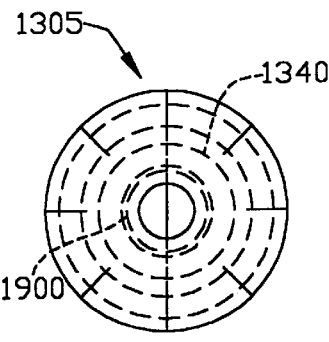
FIG. 81 is a top plan view of the core portion of FIG. 79.
Figure 82:
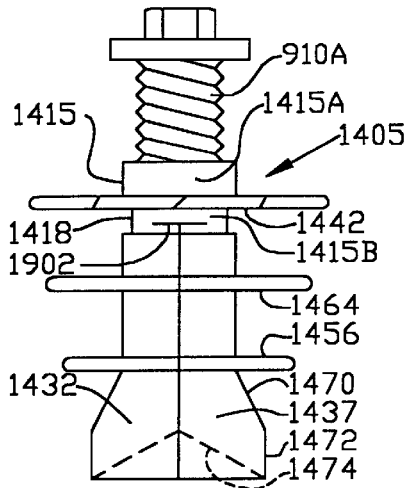
FIG. 82 is a side elevational view of another alternative embodiment of bone cement plug.

In the alternative embodiment of core 1305, shown in FIGS. 79–81, the core structure is similar to the core structure shown in FIGS. 76–78, except that the aforementioned distal protrusions 1232, 1233, 1237 and 1238 of the embodiment of FIGS. 76–78 are replaced by thicker, substantially non-deformable protrusions 1332, 1337 which, before expansion, form a distal flange 1340. The protrusions 1332, 1337 are of equal thickness, and are at least twice as thick as proximal annular flange 1342, and at least twice as thick as each of the intermediate flanges 1356, 1364. When the bone cement plugs are formed of relatively soft material, the flanges 1139 and 1140 of the embodiment shown in FIG. 73, and the flange 1240 of the embodiment shown in FIG. 76, may deform excessively. The flange 1340 of the embodiment shown in FIG. 79 is provided with a thickness which resists such deformation upon impingement on the bone canal wall. The embodiment of FIGS. 79–81 is installed similarly to, and serves the same purpose as, the previously-described embodiment of FIGS. 57–61.

The alternative embodiment of core 1405 is shown in FIGS. 82–88. In this embodiment, there are three annular flanges, a proximal flange 1442, a distal flange 1456, and an intermediate flange 1464, each formed by at least two laterally-extending protrusions, as described above. A base portion 1415 includes a first portion 1415A, which extends proximally from proximal flange 1442, and a second portion 1415B, which extends distally from proximal flange 1442. The base section portion 1415B is provided with an annular groove 1418.

At a distal end of core 1405, first and second protrusions 1432, 1437 are provided which, prior to expansion (FIGS. 82 and 83), form (i) a generally frusto-conically shaped portion 1470, and (ii) a cylindrically shaped portion 1472 extending distally from the frusto-conically shaped portion 1470. The protrusions 1432, 1437 form, internally thereof, a conically-shaped cavity 1474. The distal protrusions 1432, 1437 are relatively bulky and resist deformation. The distal edges of the protrusions 1432, 1437 are relatively sharp and engage the irregularity of the bone canal wall. Because of the conically-shaped cavity 1474, the edges of protrusions 1432, 1437 point distally when the edges engage the bone wall. With the edges pointed distally, the expanded core better resists distal migration of the bone cement plug.

The base portion 1415 is provided with a threaded bore 1420 (FIGS. 83 and 88) adapted to receive the aforementioned expander screw 910A. The insertion tool 1000, described above and shown in FIGS. 64–70, may be used to place and set the bone cement plug of FIGS. 82, 83, 87 and 88.

Figure 84:
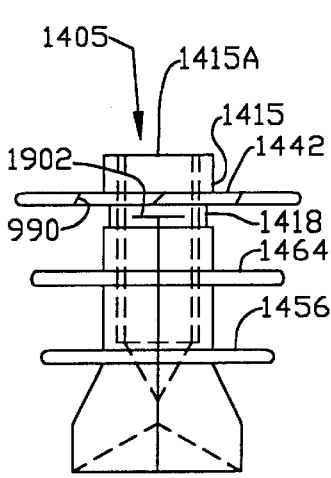
FIG. 84 is a side elevational view of a core portion of the bone cement plug of FIG. 82.
Figure 87:
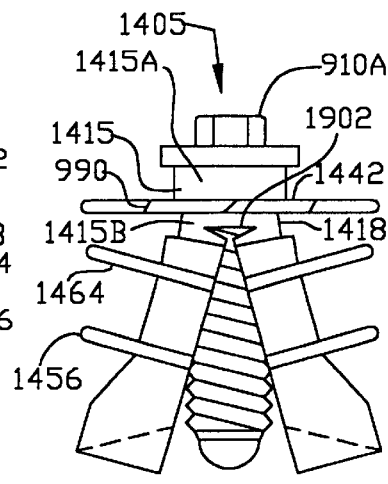
FIG. 87 is a side elevational view of the bone cement plug of FIG. 82, shown in expanded condition.
Figure 83:
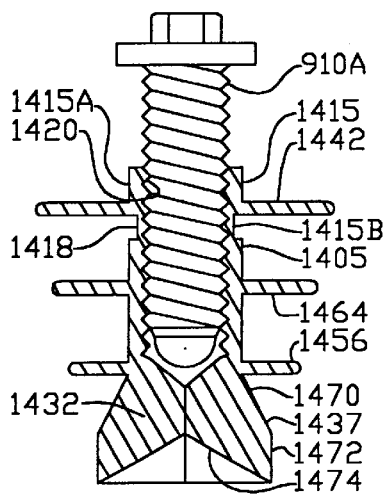
FIG. 83 is a sectional, partly side elevational, view, of the bone cement plug of FIG. 82.
Figure 85:
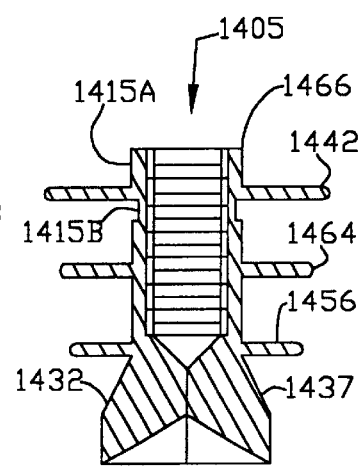
FIG. 85 is a sectional view of the core portion of FIG. 84.
Figure 88:
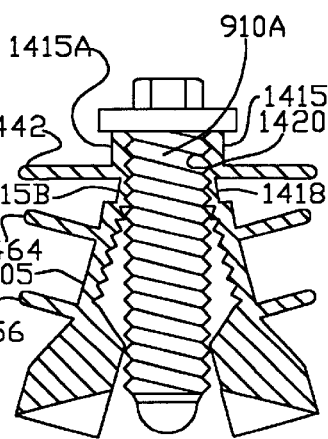
FIG. 88 is a sectional, partly side elevational view, of the bone cement plug of FIG. 83, shown in expanded condition.
Figure 86:
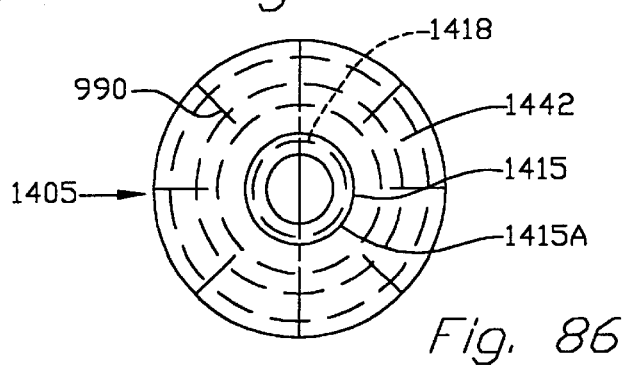
FIG. 86 is a top plan view of the core portion of FIG. 84.

In FIGS. 84 and 85, the threaded bore 1420 of the core 1405 shown in FIG. 83 is replaced with an alternative bore wall configuration, e.g., with a ribbed wall capable of receiving a distally-driven expander member 910.

Figure 89:
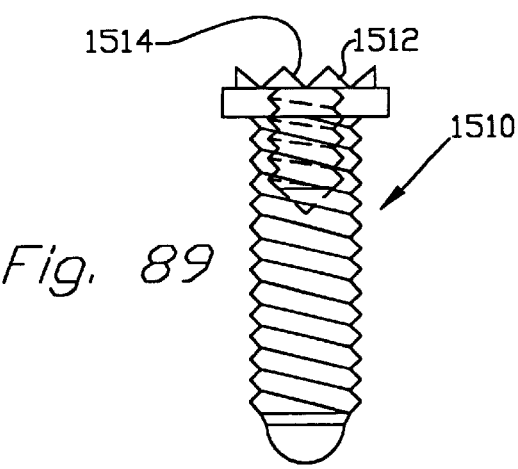
FIG. 89 is a side elevational view of an alternative embodiment of expander screw.
Figure 90:
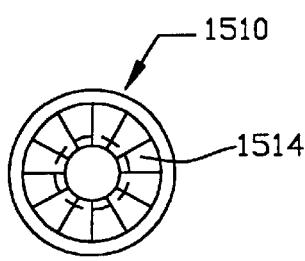
FIG. 90 is a top plan view of the expansion screw of FIG. 89.
Figure 91:
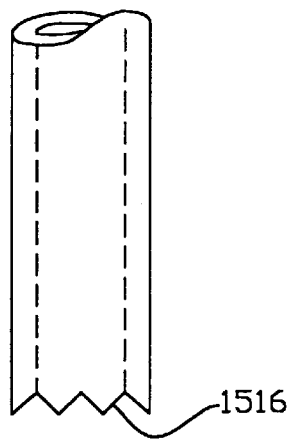
FIG. 91 is a side elevational view of a distal portion of another alternative embodiment of insertion tool, of a type used in conjunction with the expander screw of FIGS. 89 and 90.
Figure 92:
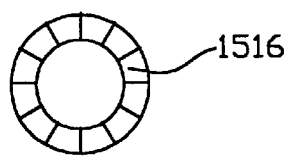
FIG. 92 is a distal end view of the insertion tool of FIG. 91.

In FIGS. 89 and 90, there is shown an alternative expander screw 1510 similar to the expander screw 910A previously discussed, but having, in place of screw head 974 (FIG. 62), a crown portion 1512 having a shaped proximal surface 1514 complementary to a tool sleeve distal end surface 1516 (FIGS. 91 and 92). In operation, the tool sleeve distal end surface 1516 is engaged with the expander screw proximal surface 1514 in much the same manner as previously described with respect to tool socket 1052 and expander screw head 974.

Figure 93:
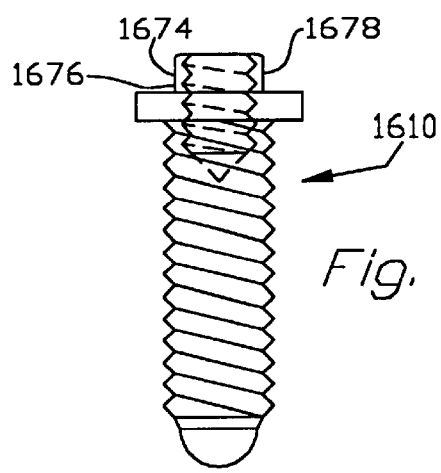
FIG. 93 is a side elevational view of still another alternative embodiment of expander screw.
Figure 94:
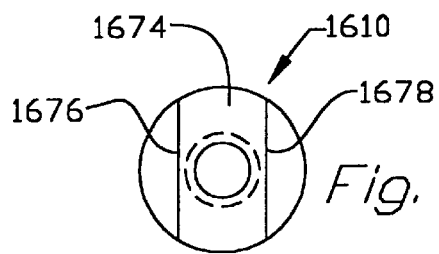
FIG. 94 is a top plan view of the expander screw of FIG. 93.
Figure 95:
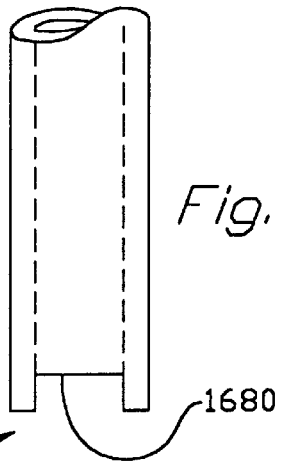
FIG. 95 is a side elevational view of a distal portion of still another alternative embodiment of insertion tool, of a type used in conjunction with the expander screw of FIGS. 93 and 94.
Figure 96:
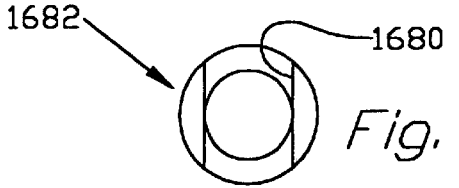
FIG. 96 is a distal end view of the insertion tool of FIG. 95.
Figure 97:
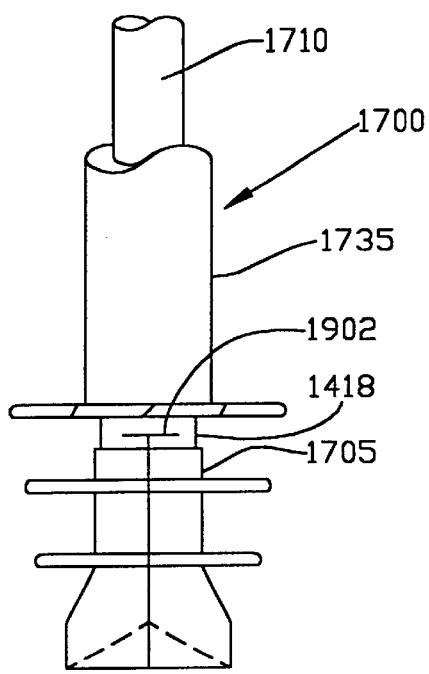
FIG. 97 is a side elevational view of the core portion of FIG. 84 in combination with an alternative expander member and an alternative tool.

In FIGS. 93 and 94, there is shown a further alternative expander screw 1610, similar to the embodiment of expander screw 910A shown in FIGS. 62 and 63, but in which a head portion 1674 is provided with two parallel flat sides 1676, 1678 received by a keyway slot 1680 in a tool sleeve distal end 1682. In operation, the tool sleeve distal end 1682 (FIGS. 95 and 96) is engaged with the expander screw head portion 1674 in essentially the same manner as previously described with respect to tool socket 1052 and expander screw head 974.

In FIGS. 97–101, there is shown an alternative embodiment of bone cement plug assembly 1700 which includes a core 1705 similar to core 1405, but in which teeth 1722 comprise ratchet teeth rather than screw threads. The expander member 910 may be any of the above-described expander members, but provided with ratchet teeth, rather than screw threads. Alternatively, as shown in FIGS. 98–101, the expander member 910 may, in this embodiment, comprise an expansion plug 910B provided with ratchet teeth 1770 complementary to ratchet teeth 1722.

Figure 98:
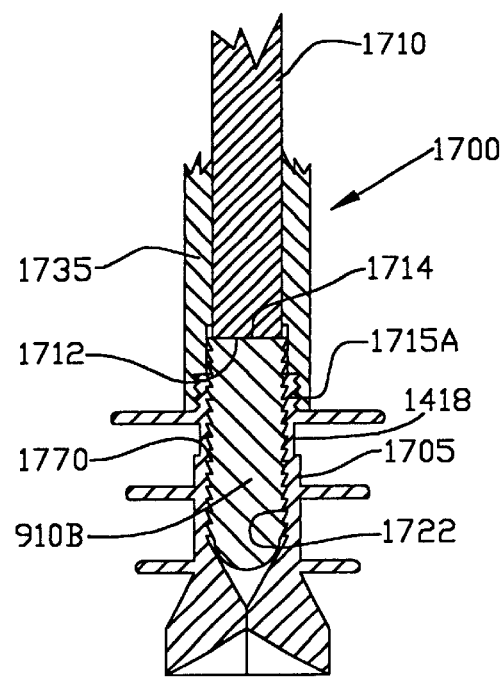
FIG. 98 is a sectional view of the bone cement plug and insertion tool of FIG. 97.
Figure 99:
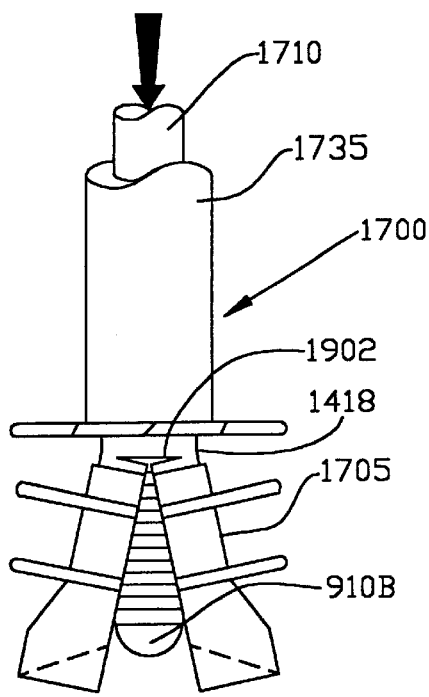
FIG. 99 is similar to FIG. 97, but showing the bone cement plug in an expanded condition.
Figure 100:
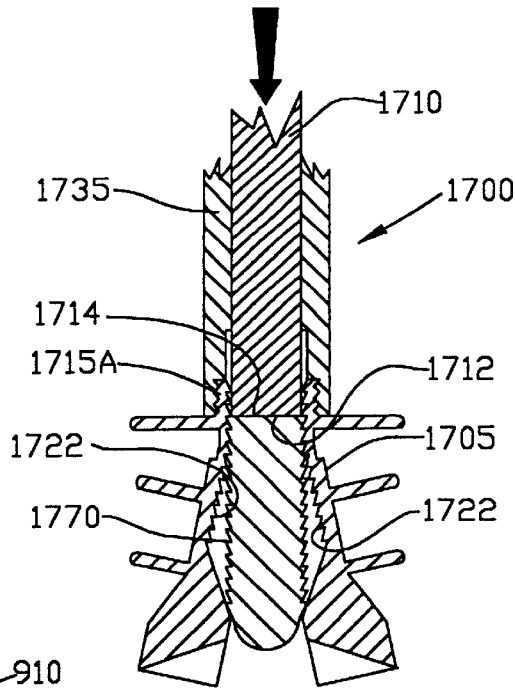
FIG. 100 is similar to FIG. 98, but showing the bone cement plug in an expanded condition.
Figure 101:
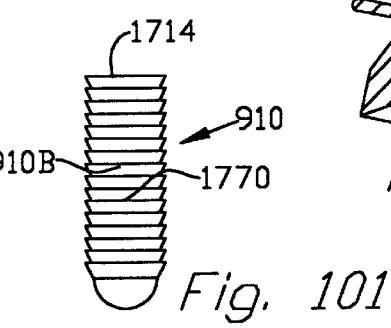
FIG. 101 is a side elevational view of the expander member of FIGS. 98–100.

Inasmuch as there is no need to turn the expander member 910B in the core 1705, a tool rod 1710 may be provided with a flat distal end 1712 for pushing against a flat proximal surface 1714 of expander member 910B, as shown in FIGS. 98 and 100. To stabilize rod distal end 1712 on expander member proximal surface 1714, a base portion 1715A of core 910B may be threaded to engage an internally threaded tool sleeve 1735.

In operation, the sleeve 1735 is threadedly engaged with the core base portion 1715A. The rod 1710 is pushed through sleeve 1735 until surfaces 1712, 1714 are in contact. Continued pushing of rod 1710 advances expander member 910B into core 1705 so as to expand the core into secure engagement with the bone canal wall. The sleeve 1735 is then unscrewed from core base portion 1715A and the sleeve and rod 1710 are disengaged from cement plug 1700.

In FIGS. 102–105, there is shown an alternative embodiment of bone cement plug 1800 including a core 1805 and an expander member 1810. The core 1805 comprises a substantially cylindrically-shaped base portion 1815 at a distal end of the core, defining a bore 1820 having internal teeth 1822 therein. The bore 1820 and teeth 1822 extend proximally from distal end 1824 of base portion 1815. First and second leg portions 1830, 1835 upstand from base portion 1815. The leg portions 1830, 1835 define an extension 1820A of bore 1820 to a proximal end 1826 of core 1805. The bore extension 1820A is provided with an extension 1822A of the bore internal teeth 1822.

As described above, the core 1805 is provided with protrusions which, prior to expansion, define a circular distal flange 1840, a proximal flange 1842, and one or more intermediate flanges 1856, 1864.

The expander member 1810 comprises a shaft 1866 having teeth 1870 thereon which are complementary to internal teeth 1822, 1822A of bores 1820, 1820A. A wedge-shaped body portion 1868 extends proximally and outwardly from a proximal end of shaft 1866. A head 1874 is fixed on a proximal surface 1872 of wedge body portion 1868.

In operation, a tool, as described above, having a socket at a distal end thereof engages the head 1874. Turning of the tool turns the threaded shaft 1866 in threaded bores 1820, 1820A. When wedge body portion 1868 is advanced into contact with leg portions 1830, 1835, the wedge body portion forces leg portions 1830, 1835 apart at their proximal ends. The farther wedge body portion 1868 is advanced into core 1805, the further apart the leg portions 1830, 1835 are driven, until the flanges 1842, 1864, 1856 and 1840 are in secure contact with the bone canal wall. It will be apparent that in this embodiment, ratchet teeth (similar to those shown in FIGS. 97–101) may be substituted for threads 1820, 1820A, 1822, and 1822A.

Referring again to FIGS. 57, 59, 61, 71, 72, 73–81 and 102–105, it will be seen that the respective cores preferably are provided with annular grooves 1900 similar to the grooves 1418 in the embodiments shown in FIGS. 82–88 and 97–100. The grooves 1418, 1900, located proximate a junction of the base portion and the leg portions, reduce the thickness of the core wall to allow the leg portions to easily flex without requiring application of excessive force.

When it is found that the annular grooves 1418, 1900 fail to provide the degree of flexibility required, as may be caused, for example, by the use of a relatively stiff core material, the leg portions may be rendered more easily wedged apart by the provision of transverse slits 1902 at the closed end of the division between the first and second leg portions. The longer the slit 1902, the more easily the leg portions can be wedged apart.

It will be appreciated that, while in the foregoing discussion, the cores have been described and shown to have two opposing leg portions, more than two leg portions could also be provided.

It will further be appreciated that the principles and features of the present invention may be employed in various and numerous embodiments without departing from the scope of the present invention. Thus, it will be understood that the present invention is by no means limited to the particular construction herein disclosed and/or shown in the drawings, but also comprises any modifications or equivalents within the scope of the claims.

ADVANTAGES OF THE INVENTION

Numerous advantages are achieved through the provision and use of the present invention.

For one thing, the present invention provides a bone cement plug which improves upon the bone cement plugs previously known in the art.

For another thing, the present invention provides an improved bone cement plug which is easy to deploy at the desired depth in the bone canal, effective in closing off that bone canal and, in the event that the bone cement plug subsequently needs to be removed, easy to retrieve from the depth of the bone canal.

And the present invention provides a bone cement plug which is bio-compatible with the patient, and which is inexpensive to produce.

Also, the present invention provides an insertion tool for deploying the bone cement plug at the desired depth in the bone canal and, in the event that the bone cement plug subsequently needs to be removed, an extraction tool for retrieving the bone cement plug from the depth of the bone canal.

Furthermore, the present invention provides an improved method for closing off the distal end of a bone canal.

What is claimed is:

1. A core for forming a bone cement plug for deployment in a bone canal, said core comprising:

a base portion defining a bore having internal teeth therein and extending axially and distally from a proximal end of said base portion;

a first leg portion depending from and extending distally from said base portion, said first leg portion having a first substantially rigid protrusion at a distal end thereof extending outwardly from an outside wall of said first leg portion through a first arc and having a first substantially flexible flange proximal to said first protrusion; and a second leg portion depending from and extending distally from said base portion, said second leg portion having a second substantially rigid protrusion at a distal end thereof extending outwardly from an outside wall of said second leg portion through a second arc and oppositely to said first arc and having a second substantially flexible flange proximal to said second protrusion;

said base portion toothed bore being adapted to receive an expander member to wedge apart said first and second leg portions to expand said core widthwise to secure said core in the bone canal.

2. A core according to claim 1 comprising an annular flange proximate a proximal end of said core and extending outwardly from said core base portion and engageable with a wall of the bone canal.

3. A core according to claim 2 comprising a further pair of opposed protrusions disposed between said first and second protrusions and said annular flange.

4. A core according to claim 3 wherein said leg portions, prior to expansion, abut each other and together form a substantially cylindrical configuration of substantially the same diameter as a diameter of said base portion.

5. A core according to claim 4 wherein said leg portions, after expansion, are separated from each other and extend from said base portion in diametrically-opposed outwardly directions to assume a generally oval configuration in the bone canal.

6. A core according to claim 4 wherein said further pair of opposed protrusions, prior to expansion, together form an annular flange having a diameter no larger than a diameter of said proximal end annular flange and no less than a diameter of a distal flange formed by said first and second protrusions.

7. A core according to claim 6 comprising a third protrusion proximate and spaced from said distal end of said first leg portion and extending outwardly from said outside wall of said first leg portion through a third arc substantially co-extensive with said first arc and with the extent of said first protrusion, and a fourth protrusion proximate and spaced from said distal end of said second leg portion and extending outwardly from said outside wall of said second leg portion through a fourth arc substantially co-extensive with said second arc and with the extent of said second protrusion.

8. A core according to claim 6 comprising a still further pair of opposed protrusions disposed between said proximal end annular flange and said further pair of opposed protrusions, said still further pair of opposed protrusions, prior to expansion, together forming an annular flange having a diameter no larger than a diameter of said proximal end annular flange, and no less than a diameter of said annular flange formed by said further pair of opposed protrusions.

9. A core according to claim 2 wherein said first and second protrusions are of substantially equal thickness.

10. A core according to claim 9 wherein said thickness is at least twice a thickness of said annular flange.

11. A core according to claim 2 wherein there is formed in said base portion, adjacent to and distally of said annular flange, an annular groove.

12. A core for forming a bone cement plug for deployment in a bone canal, said core comprising:

a base portion defining a bore having internal teeth therein and extending axially and distally from a proximal end of said base portion;

a first leg portion depending from and extending distally from said base portion, said first leg portion having a first protrusion at a distal end thereof extending outwardly from an outside wall of said first leg portion through a first arc; and a second leg portion depending from and extending distally from said base portion, said second leg portion having a second protrusion at a distal end thereof extending outwardly from an outside wall of said second leg portion through a second arc and oppositely to said first arc;

an annular flange proximate a proximal end of said core and extending outwardly from said core base portion and engageable with a wall of the bone canal; and a further pair of opposed protrusions disposed between said first and second protrusions and said annular flange;

said base portion toothed bore being adapted to receive an expander member to wedge apart said first and second leg portions to expand said core widthwise to secure said core in the bone canal;

said leg portions, prior to expansion, abut each other and together form a substantially cylindrical configuration of substantially the same diameter as a diameter of said base portion;

said further pair of opposed protrusions, prior to expansion, together form an annular flange having a diameter no larger than a diameter of said proximal end annular flange and no less than a diameter of a distal flange formed by said first and second protrusions;

a third protrusion proximate and spaced from said distal end of said first leg portion and extending outwardly from said outside wall of said first leg portion through a third arc substantially co-extensive with said first arc and with the extent of said first protrusion, and a fourth protrusion proximate and spaced from said distal end of said second leg portion and extending outwardly from said outside wall of said second leg portion through a fourth arc substantially co-extensive with said second arc and with the extent of said second protrusion;

said first and second protrusions are inclined distally to form a generally inverted saucer configuration at a distal end of said core prior to expansion of said core.

13. A core for forming a bone cement plug for deployment in a bone canal, said core comprising:

a base portion defining a bore having internal teeth therein and extending axially and distally from a proximal end of said base portion;

a first leg portion depending from and extending distally from said base portion, said first leg portion having a first protrusion at a distal end thereof extending outwardly from an outside wall of said first leg portion through a first arc;

a second leg portion depending from and extending distally from said base portion, said second leg portion having a second protrusion at a distal end thereof extending outwardly from an outside wall of said second leg portion through a second arc and oppositely to said first arc; and an annular flange proximate a proximal end of said core and extending outwardly from said core base portion and engageable with a wall of the bone canal said base portion toothed bore being adapted to receive an expander member to wedge apart said first and second leg portions to expand said core widthwise to secure said core in the bone canal;

said first and second protrusions are of substantially equal thickness;

said thickness is at least twice a thickness of said annular flange;

said first and second protrusions, prior to expansion, form a generally frusto-conically shaped portion extending distally from said leg portions, and a cylindrical portion extending distally from said frusto-conically shaped portion, said protrusions forming, internally thereof, a conically-shaped cavity.

14. A core for forming a bone cement plug for deployment in a bone canal, said core comprising:

a base portion defining a bore having internal teeth therein and extending axially and distally from a proximal end of said base portion;

a first leg portion depending from and extending distally from said base portion, said first leg portion having a first protrusion at a distal end thereof extending outwardly from an outside wall of said first leg portion through a first arc;

a second leg portion depending from and extending distally from said base portion, said second leg portion having a second protrusion at a distal end thereof extending outwardly from an outside wall of said second leg portion through a second arc and oppositely to said first arc; and an annular flange proximate a proximal end of said core and extending outwardly from said core base portion and engageable with a wall of the bone canal;

said base portion toothed bore being adapted to receive an expander member to wedge apart said first and second leg portions to expand said core widthwise to secure said core in the bone canal;

said first and second protrusions are of substantially equal thickness;

said thickness is at least twice a thickness of said annular flange;

said first and second protrusions, prior to expansion, form a generally frusto-conically shaped portion extending distally from said leg portions, and a cylindrical portion extending distally from said frusto-conically shaped portion, said protrusions forming, internally thereof, a conically-shaped cavity;

a distal end of said cylindrical portion is of a substantially sharp configuration.

15. A bone cement plug for deployment in a bone canal, said plug comprising:

a core comprising:

a base portion defining a bore having internal teeth therein and extending axially and distally from a proximal end of said base portion;

a first leg portion depending from and extending distally from said base portion, said first leg portion having a first substantially rigid protrusion at a distal end thereof extending outwardly from an outside wall of said first leg portion through a first arc of about 180 degrees and having a first substantially flexible flange proximal to said first protrusion; and a second leg portion depending from and extending distally from said base portion, said second leg portion having a second substantially rigid protrusion at a distal end thereof extending outwardly from an outside wall of said second leg portion through a second arc of about 180 degrees and oppositely to said first arc and having a second substantially flexible flange proximal to said second protrusion;

said base portion toothed bore having an internally tapered distal end and being adapted to receive an expander member to wedge apart said first and second leg portions to expand said core widthwise to secure said core in the bone canal; and said expander member comprising:

a generally cylindrically-shaped body having a distal end for entering said bore, and a proximal end at which is disposed connecting means for connection to a tool, said expander member having external teeth engageable with said core toothed bore for said wedging apart of said first and second leg portions.

16. A bone cement plug according to claim 15 wherein said distal end of said expander member is rounded.

17. A bone cement plug according to claim 15 wherein said connecting means at said proximal end of said expansion device comprises a selected one or more of (i) internal threads formed in a bore in a proximal end of said expansion device, said internal threads being complementary to external threads of a tool end, (ii) a head having a configuration complementary to a socket configuration of a tool end, (iii) a crown having a proximal surface complementary to a distal surface of a tool end, and (iv) a flat proximal surface complementary to a flat distal surface of a tool push rod.

18. A bone cement plug according to claim 15 wherein said bore internal teeth comprise screw threads and said expander member external teeth comprise complementary screw threads.

19. A bone cement plug according to claim 15 wherein said bore internal teeth comprise ratchet teeth and said expander member external teeth comprise complementary ratchet teeth.

20. A bone cement plug for deployment in a bone canal, said plug comprising:

a core comprising:

a base portion defining a bore having internal teeth therein and extending axially and proximally from a distal end of said base portion;

first and second leg portions upstanding from said base portion, said leg portions defining an extension of said bore to a proximal end of said plug, said extension of said bore being provided with an extension of said bore internal teeth;

substantially rigid protrusions extending outwardly from outside walls of said leg portions and substantially flexible flanges extending outwardly from outside walls of said leg portions proximal to said first protrusion;

said bore extension and said bore being adapted to receive an expander member to wedge apart said leg portions to expand said core, and thereby said protrusions widthwise, to secure said core in the bone canal; and said expander member comprising:
a shaft having external teeth complementary to said internal teeth of said bore extension and said bore;
a wedge-shaped body portion extending proximally and outwardly from a proximal end of said shaft; and
connector means disposed at a proximal end of said wedge-shaped portion for interconnection with a tool.

21. A bone cement plug assembly comprising:
a core comprising:
a base portion defining a bore having internal teeth therein and extending axially and distally from a proximal end of said base portion;
a first leg portion depending from and extending distally from said base portion, said first leg portion having a first substantially rigid protrusion at a distal end thereof extending outwardly from an outside wall of said first leg portion through a first arc of about 180 degrees and having a first substantially flexible flange proximal to said first protrusion; and
a second leg portion depending from and extending distally from said base portion, said second leg portion having a second substantially rigid protrusion at a distal end thereof extending outwardly from an outside wall of said second leg portion through a second arc of about 180 degrees and oppositely to said first arc and having a second substantially flexible flange proximal to said second protrusion;
said base portion toothed bore being adapted to receive an expander member to wedge apart said first and second leg portions to expand said core widthwise to secure said core in the bone canal; and said expander member comprising:
a generally cylindrically-shaped body having a distal end and a proximal end at which is disposed connecting means for connection to a tool, said expansion device having external teeth engageable with said core toothed bore for said wedging apart of said first and second leg portions; and an insertion tool comprising:
a sleeve having a distal end configuration complementary to a proximal portion of said expander member to move said expander member in said core to expand said core to secure said core in the bone canal.

22. A bone cement plug assembly according to claim 21 wherein said tool further comprises a rod disposed within said sleeve, said rod having, at a distal end thereof, means for engaging said expander member so as to selectively connect said expander member to said tool.

23. A bone cement plug assembly according to claim 22 wherein said rod means for engaging said expander member comprise external threads for engaging internal threads formed in said expander member.

24. A bone cement plug comprising:
a core comprising:
a base portion defining a threaded bore therein extending axially and distally from a proximal end of said base portion;
a first leg portion depending from and extending distally from said base portion, said first leg portion having a first substantially rigid protrusion at a distal end thereof extending outwardly from an outside wall of said first leg portion through a first arc and having a first substantially flexible flange proximal to said first protrusion; and
a second leg portion depending from and extending distally from said base portion and opposed to said first leg portion, said second leg portion having a second substantially rigid protrusion at a distal end thereof extending outwardly from an outside wall of said second leg portion through a second arc and oppositely to said first arc and having a second substantially flexible flange proximal to said second protrusion;
said base portion threaded bore being adapted to receive an expander screw to wedge apart said first and second leg portions, whereby to expand said core widthwise to secure said plug in a bone canal; and said expander screw, said expander screw comprising:
a generally cylindrically-shaped body having a distal end, and a proximal end in which is disposed a threaded bore, external threads disposed on said body, and an annular flange extending outwardly from said proximal end of said body, said screw being threadably engageable with said core threaded bore for advancement of said expander screw into said plug for said wedging apart of said first and second legs;
wherein at least one of said expander screw distal end and said core bore is of a tapered configuration operative to produce said wedging apart of said first and second leg portions upon advancement of said expander screw into said core bore.

25. A method for fixing a bone cement plug in a bone canal, the method comprising the steps of:
providing a bone cement plug for deployment in a bone canal, said bone cement plug comprising:
a core comprising:
a base portion defining a bore having internal teeth therein and extending axially and distally from a proximal end of said base portion;
a first leg portion depending from and extending distally from said base portion, said first leg portion having a first substantially rigid protrusion at a distal end thereof extending outwardly from an outside wall of said first leg portion through a first arc and having a first substantially flexible flange proximal to said first protrusion; and
a second leg portion depending from and extending distally from said base portion, said second leg portion having a second substantially rigid protrusion at a distal end thereof extending outwardly from an outside wall of said second leg portion through a second arc and oppositely to said first arc and having a second substantially flexible flange proximal to said second protrusion;

said base portion toothed bore being adapted to receive an expander member to wedge apart said first and second leg portions to expand said core widthwise to secure said core in the bone canal; and said expander member comprising:

a generally cylindrically-shaped body having a distal end, and a proximal end at which is disposed connecting means for connection to a tool, said expander member having external teeth engageable with said core toothed bore for said wedging apart of said first and second leg portions;

advancing said plug into the bone canal so that at least a portion of said plug engages the wall of the bone canal; and advancing said expander member in said plug to effect said expansion of said plug widthwise in the bone canal.

* * * * *